United States Patent
Katsumoto

(10) Patent No.: US 10,302,584 B2
(45) Date of Patent: May 28, 2019

(54) CARTRIDGE, KIT COMPRISING CARTRIDGE, ELECTRIC MEASURING APPARATUS, AND ELECTRIC MEASURING METHOD

(71) Applicant: Sony Corporation, Tokyo (JP)

(72) Inventor: Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 221 days.

(21) Appl. No.: 15/108,617

(22) PCT Filed: Dec. 26, 2014

(86) PCT No.: PCT/JP2014/006487
§ 371 (c)(1),
(2) Date: Jun. 28, 2016

(87) PCT Pub. No.: WO2015/104785
PCT Pub. Date: Jul. 16, 2015

(65) Prior Publication Data
US 2016/0327504 A1 Nov. 10, 2016

(30) Foreign Application Priority Data

Jan. 7, 2014 (JP) .................................. 2014-001064
Nov. 17, 2014 (JP) .................................. 2014-233041

(51) Int. Cl.
*B01L 3/00* (2006.01)
*G01N 27/02* (2006.01)
(Continued)

(52) U.S. Cl.
CPC ............ *G01N 27/226* (2013.01); *B01L 3/508* (2013.01); *B01L 3/5082* (2013.01);
(Continued)

(58) Field of Classification Search
CPC ............. G01N 27/226; G01N 33/4875; G01N 33/48757; B01L 3/508; B01L 3/5082;
(Continued)

(56) References Cited

U.S. PATENT DOCUMENTS 3,498,724 A * 3/1970 Hayes et al. ........... G01N 21/03
356/246
4,319,194 A  3/1982 Cardinal et al.
(Continued)

FOREIGN PATENT DOCUMENTS

| CN | 1646911 A | 7/2005 |
|---|---|---|
| CN | 201208437 Y | 3/2009 |

(Continued)

OTHER PUBLICATIONS

International Preliminary Report on Patentability dated Jul. 21, 2016 in connection with International Application No. PCT/JP2014/006487.

(Continued)

*Primary Examiner* — Robert J Eom
(74) *Attorney, Agent, or Firm* — Wolf, Greenfield & Sacks, P.C.

(57) ABSTRACT

In embodiments, there is provided a cartridge comprising a container comprising an opening and a holding portion to hold a sample and/or a reagent, an electrode disposed on a container wall of the container, and a removable separator to separate at least some of the holding portion of the container from the electrode when the removable separator is inserted into the holding portion. The cartridge may be combined in a kit with a member to insert the sample, or in an electrical measuring apparatus comprising a circuit to measure electrical characteristic(s) of a second signal, resulting from application of a first signal to the electrode, and indicative of electrical characteristic(s) of the sample and/or the reagent.

18 Claims, 15 Drawing Sheets

(51) Int. Cl.
*G01N 27/22* (2006.01)
*G01N 33/49* (2006.01)
*G01N 33/487* (2006.01)

(52) U.S. Cl.
CPC ...... *B01L 3/50825* (2013.01); *G01N 33/4875* (2013.01); *G01N 33/4905* (2013.01); *B01L 2300/042* (2013.01); *B01L 2300/0645* (2013.01); *B01L 2300/0858* (2013.01); *G01N 27/026* (2013.01)

(58) Field of Classification Search
CPC ........... B01L 3/50825; B01L 2300/042; B01L 2300/0645; B01L 2300/0858
See application file for complete search history.

(56) References Cited

U.S. PATENT DOCUMENTS

| | | | |
|---|---|---|---|
| 5,186,800 A * | 2/1993 | Dower | C12M 35/02 435/173.1 |
| 5,720,733 A | 2/1998 | Brown | |
| 2005/0282265 A1 | 12/2005 | Vozza-Brown et al. | |
| 2010/0136606 A1 | 6/2010 | Katsumoto et al. | |
| 2012/0035450 A1 | 2/2012 | Hayashi | |
| 2012/0048732 A1 | 3/2012 | Hayashi et al. | |
| 2015/0253269 A1 | 9/2015 | Katsumoto | |

FOREIGN PATENT DOCUMENTS

| | | |
|---|---|---|
| CN | 201561949 U | 8/2010 |
| CN | 202285009 U | 6/2012 |
| CN | 102928610 A | 2/2013 |
| EP | 2500726 A1 | 9/2012 |
| JP | 55-050162 A | 4/1980 |
| JP | 06-138067 A | 5/1994 |
| JP | 09-005268 A | 1/1997 |
| JP | 2007-304116 A | 11/2007 |
| JP | 2009-042141 A | 2/2009 |
| JP | 2010-181400 A | 8/2010 |
| JP | 2012-002518 A | 1/2012 |
| JP | 2012-052906 A | 3/2012 |
| JP | 2012-215460 A | 11/2012 |
| JP | 2013-253962 A | 12/2013 |
| WO | WO 99/047907 A1 | 9/1999 |
| WO | WO 00/32098 A1 | 6/2000 |
| WO | WO 2009/032309 A1 | 3/2009 |

OTHER PUBLICATIONS

Chinese Office Action dated May 30, 2018 in connection with Chinese Application No. 2014800719817, and English translation thereof.

International Search Report and Written Opinion dated Mar. 31, 2015 in connection with International Application No. PCT/JP2014/006487.

Extended European Search Report dated Nov. 12, 2018 in connection with European Application No. 18193802.8.

Japanese Office Action dated Mar. 5, 2019 in connection with Japanese Application No. 2014-233041, and English translation thereof.

Chinese Office Action dated Feb. 20, 2019 in connection with Chinese Application No. 201480071981.7, and English translation thereof.

* cited by examiner

[Fig. 1]
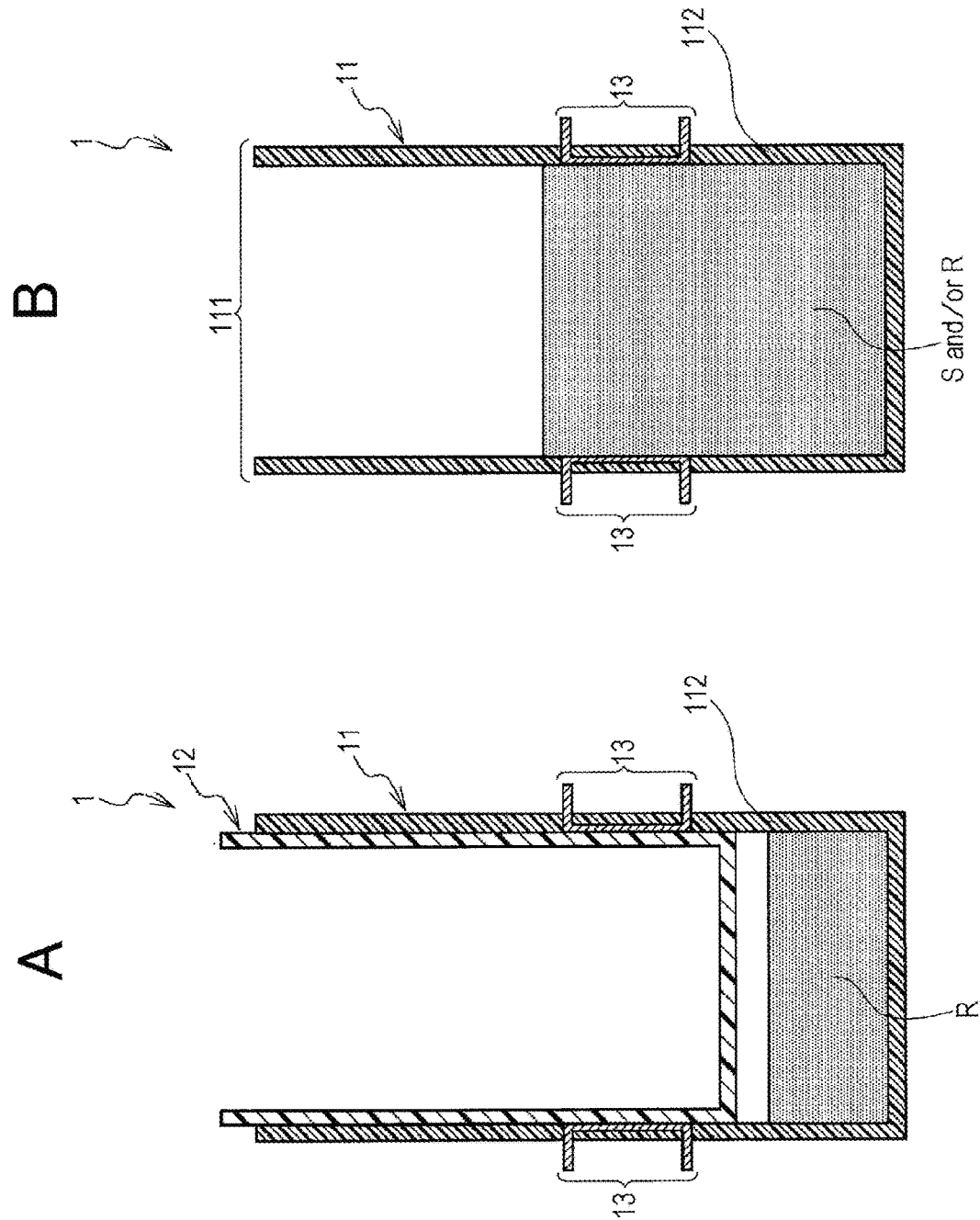

[Fig. 2]
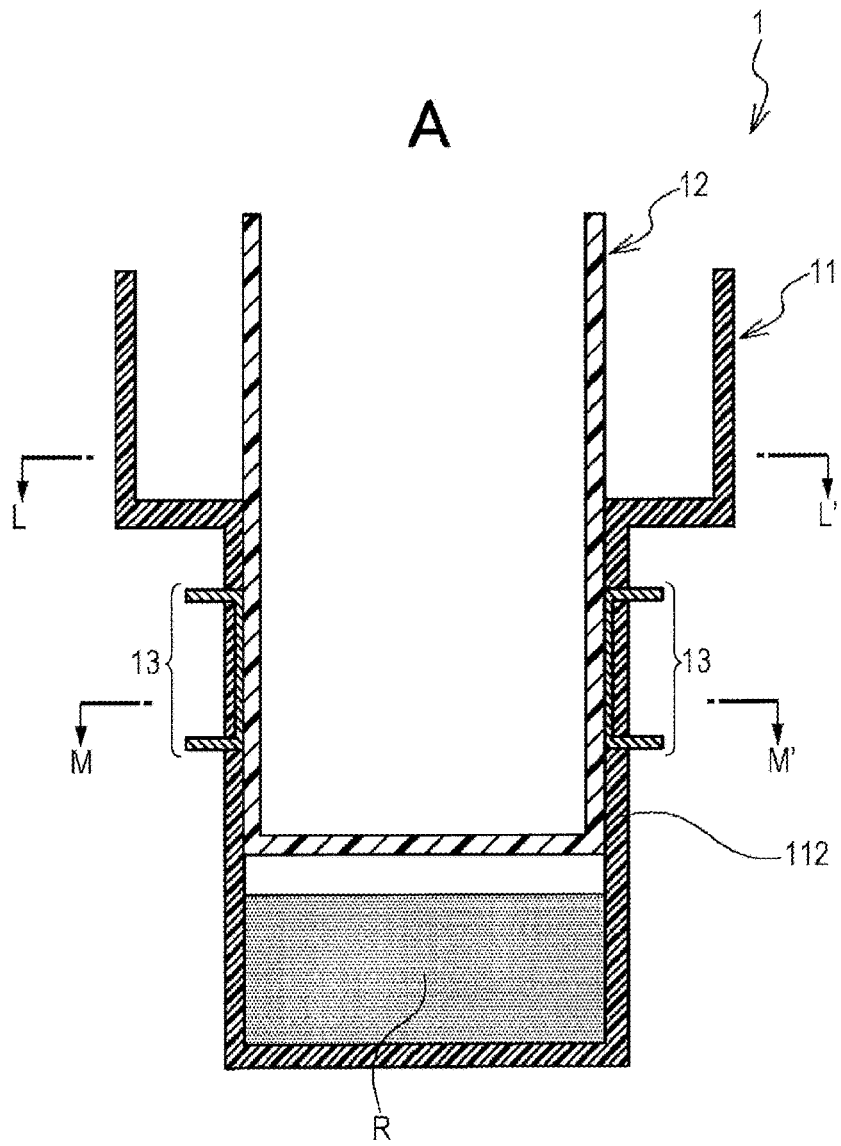
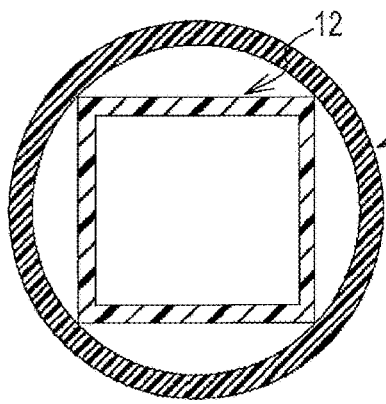
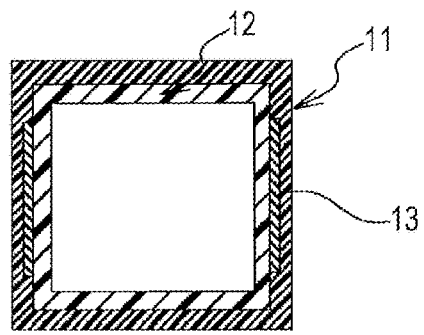

[Fig. 3]
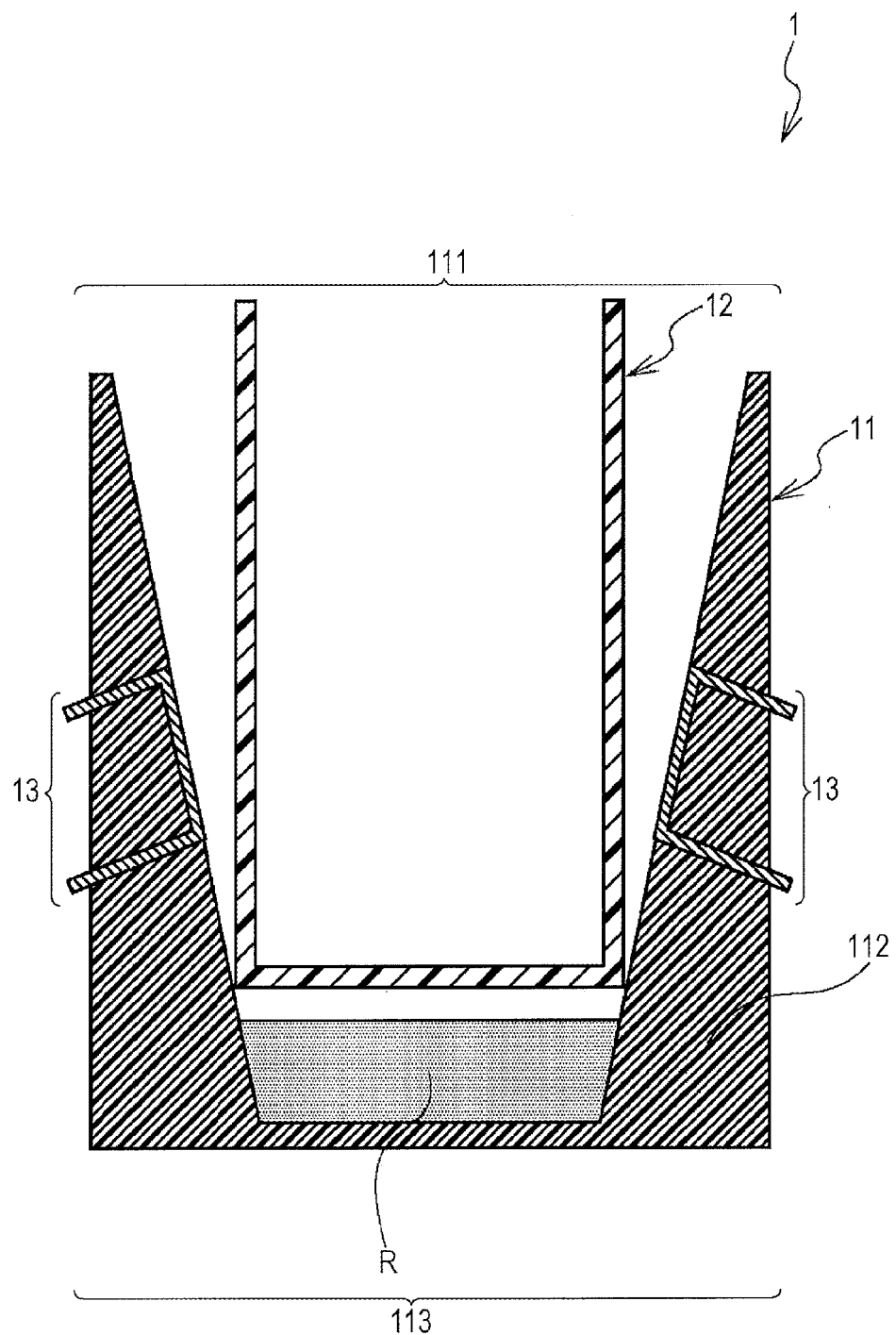

[Fig. 4]
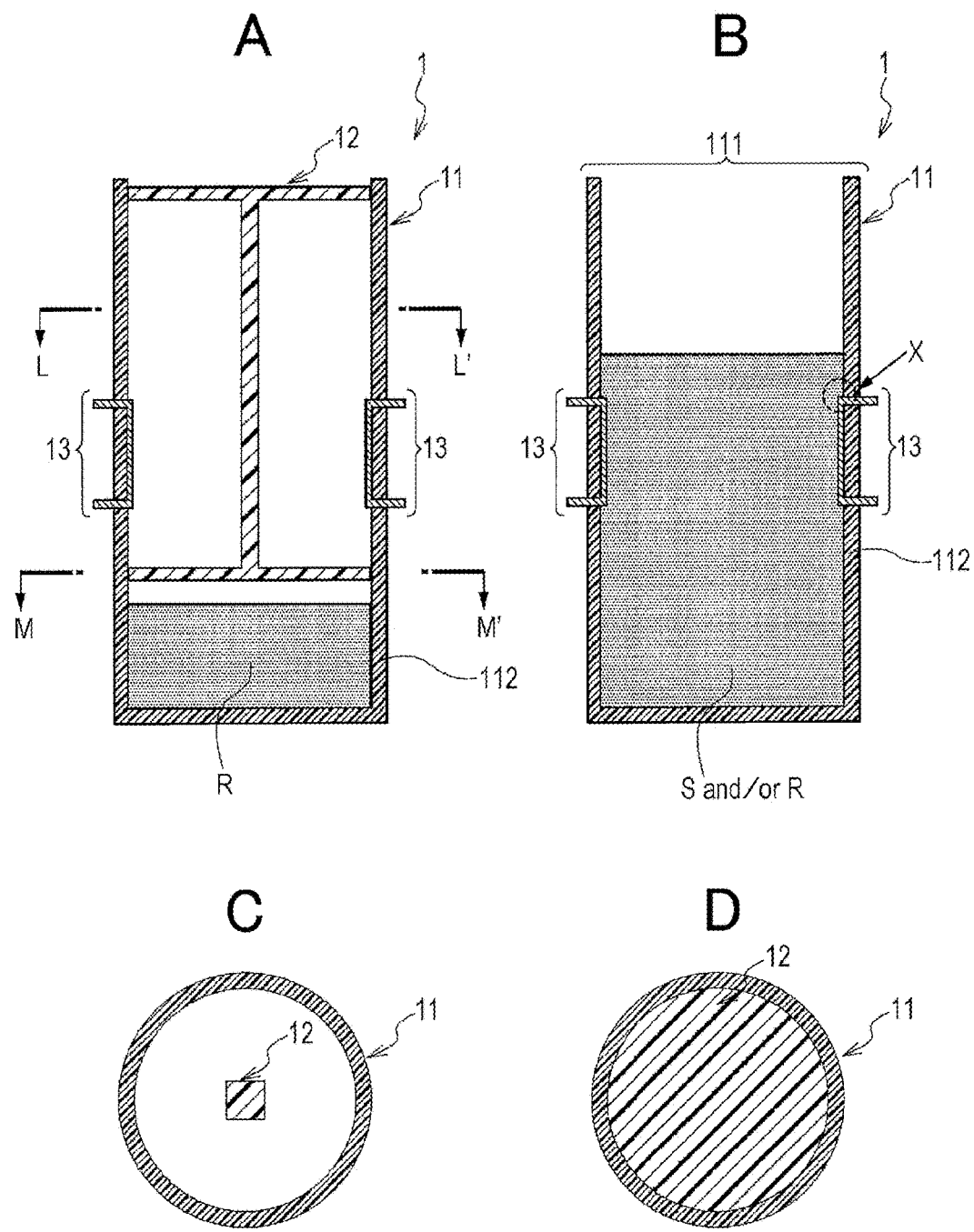

[Fig. 5]
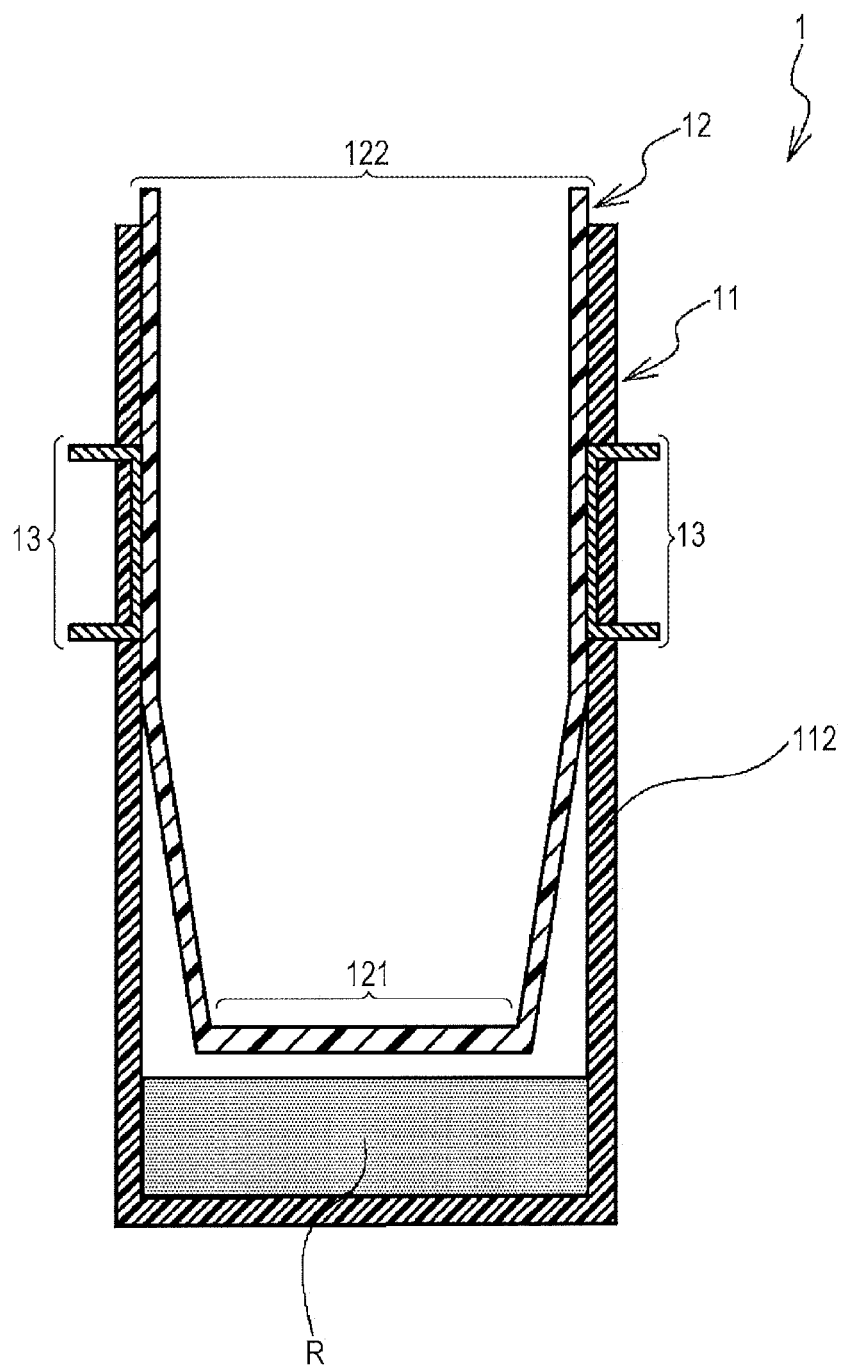

[Fig. 6]
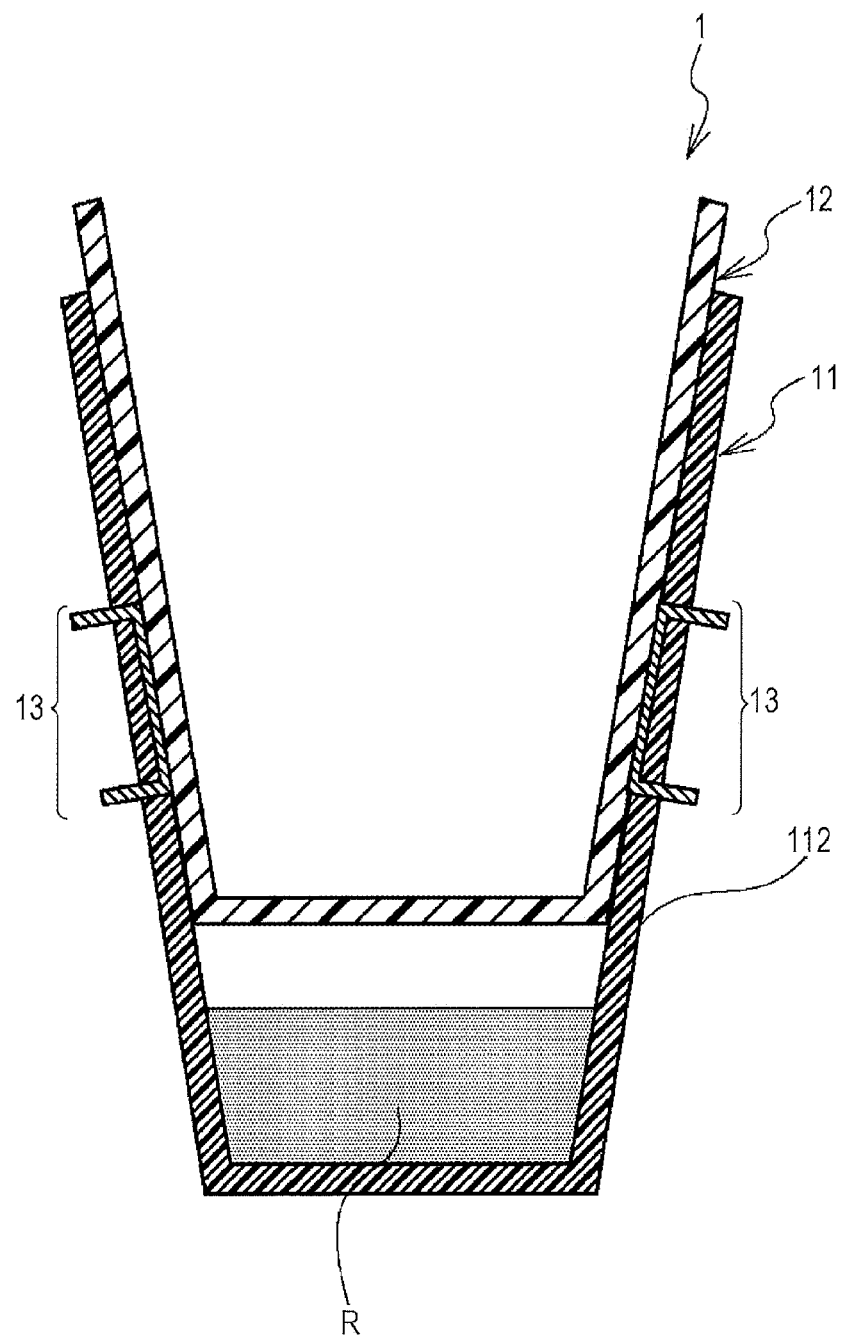

[Fig. 7]
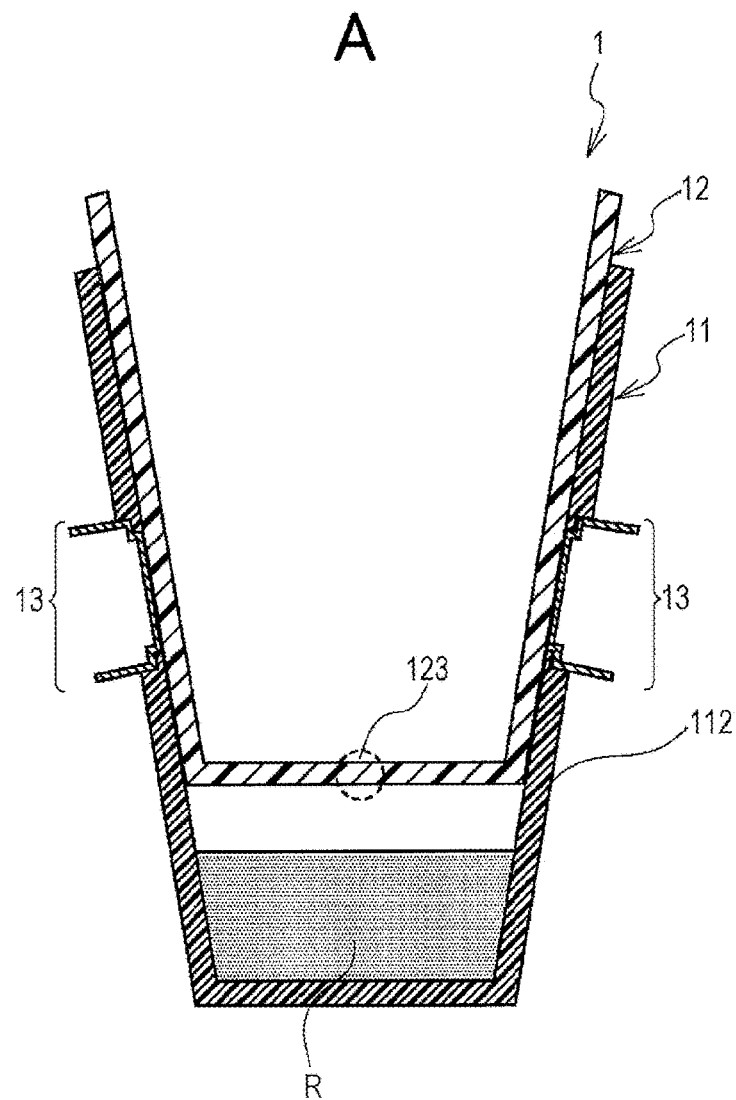
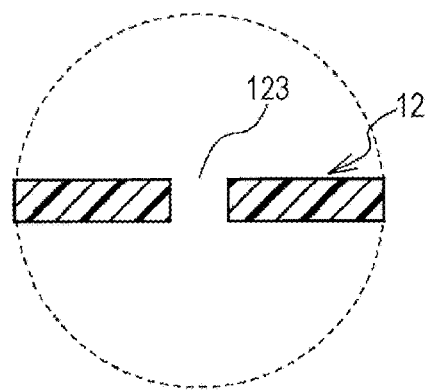
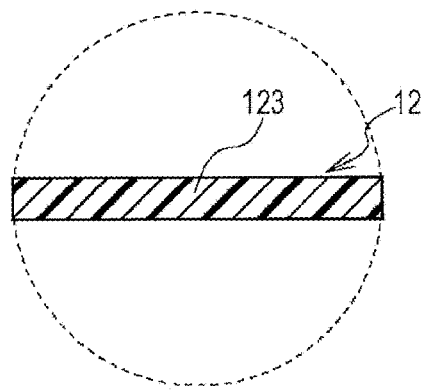

[Fig. 8]
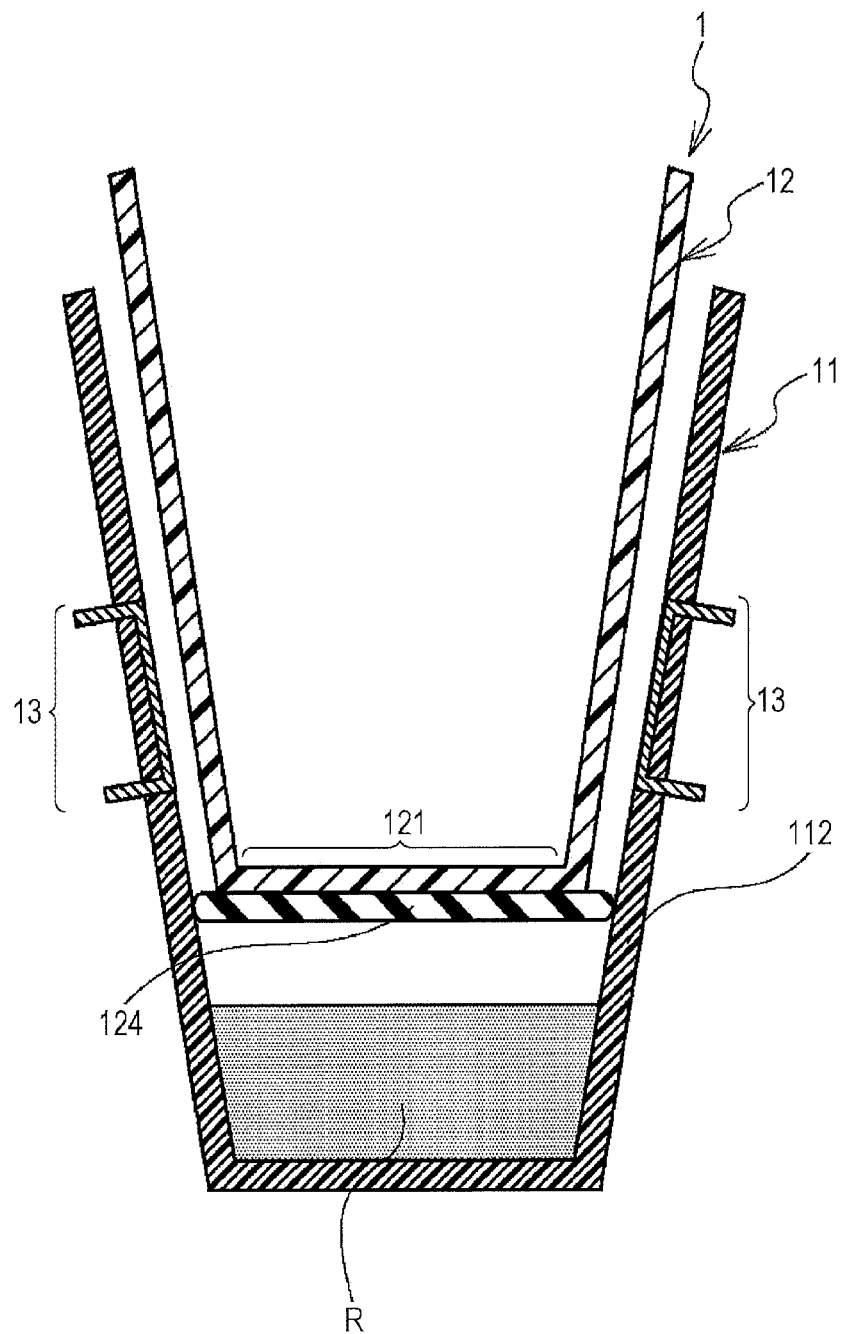

[Fig. 9]
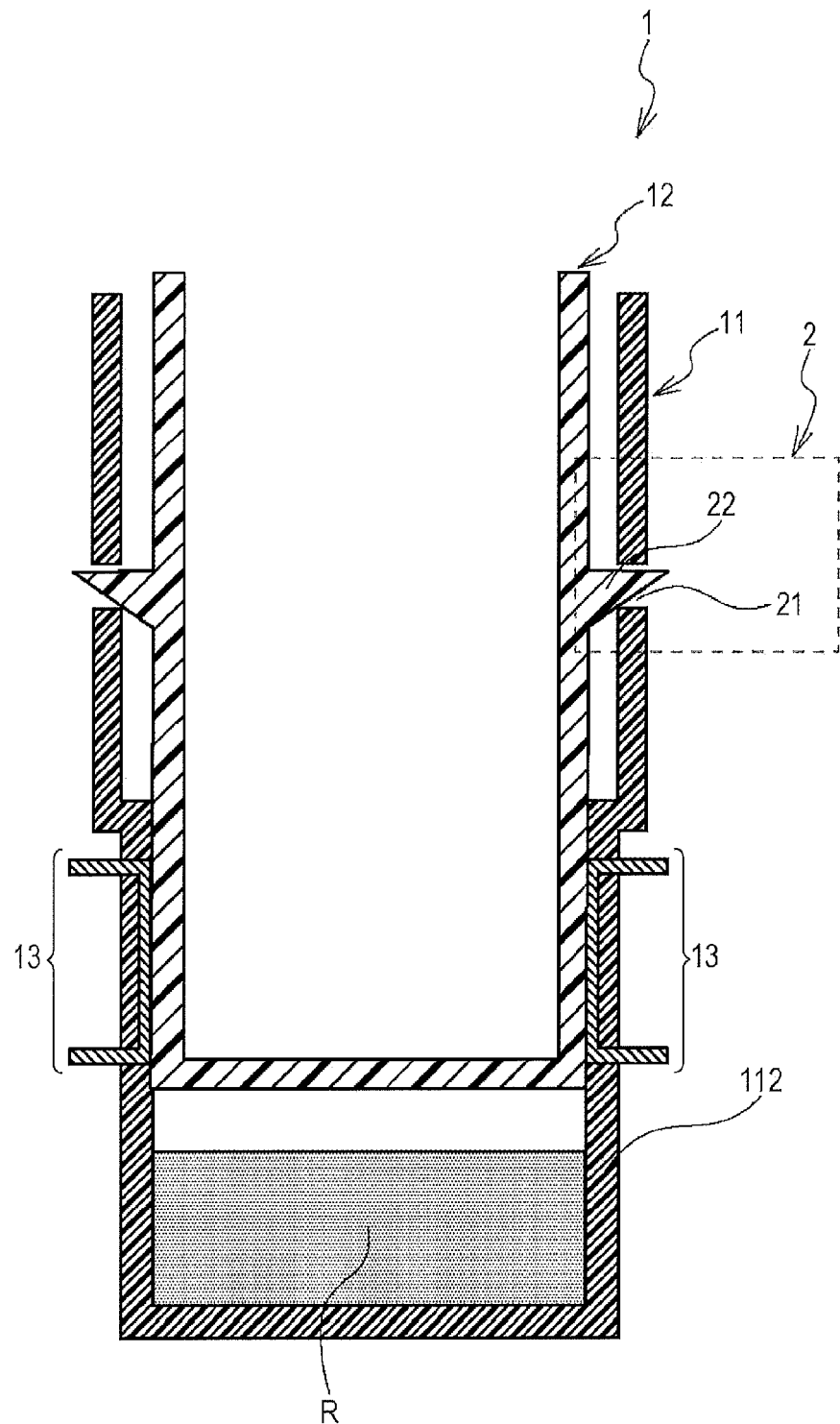

[Fig. 10]
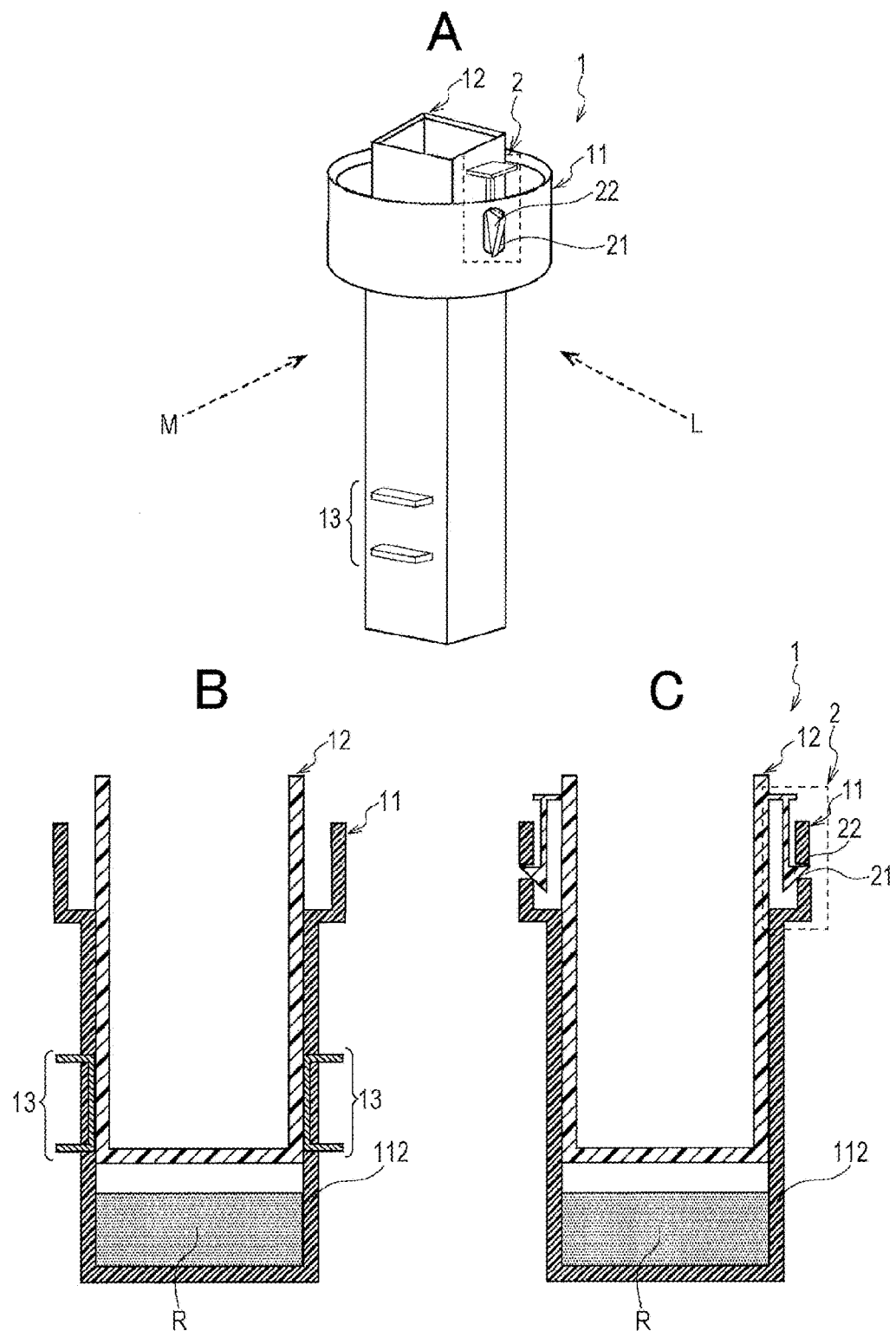

[Fig. 11]
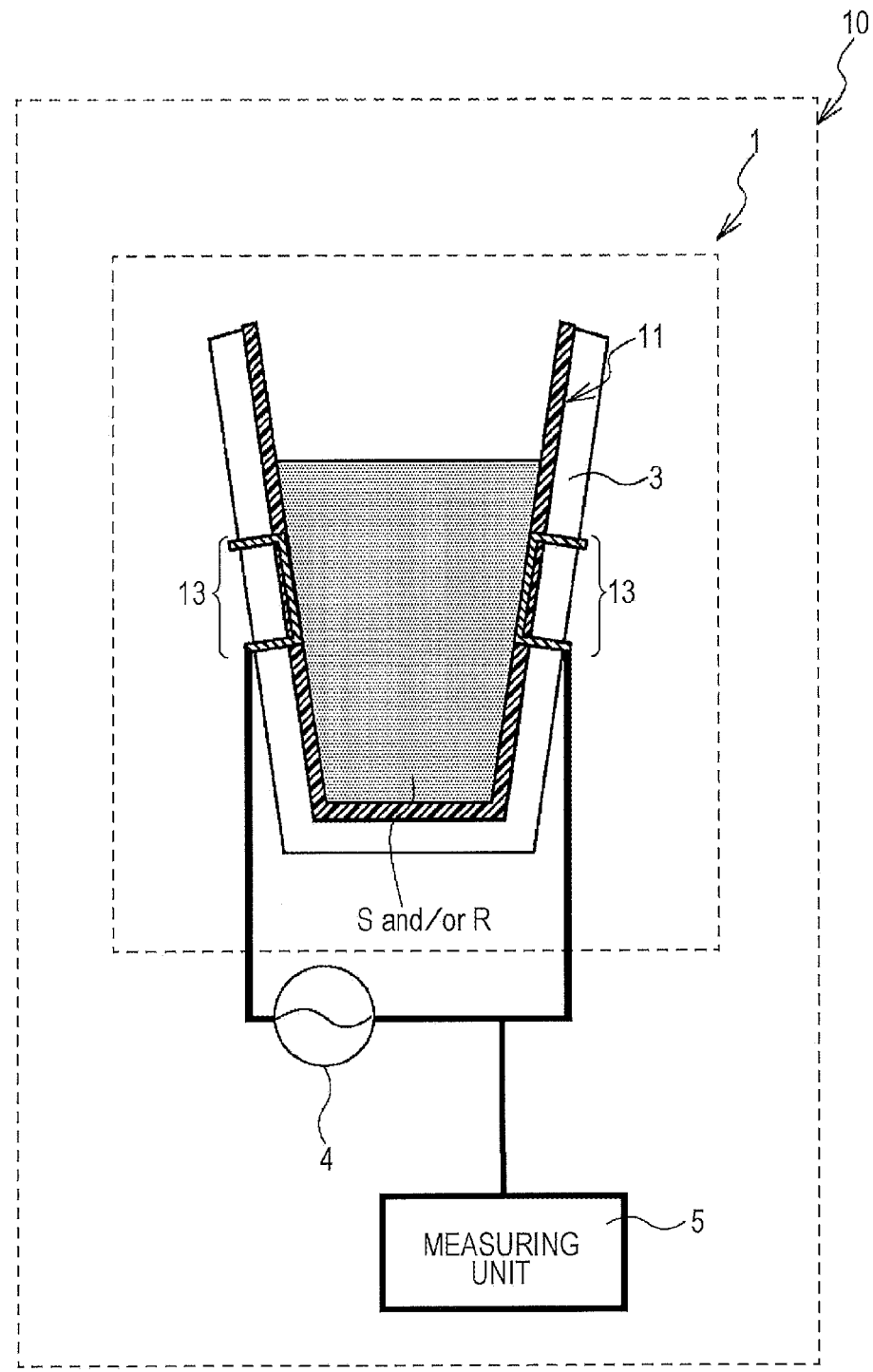

[Fig. 12]
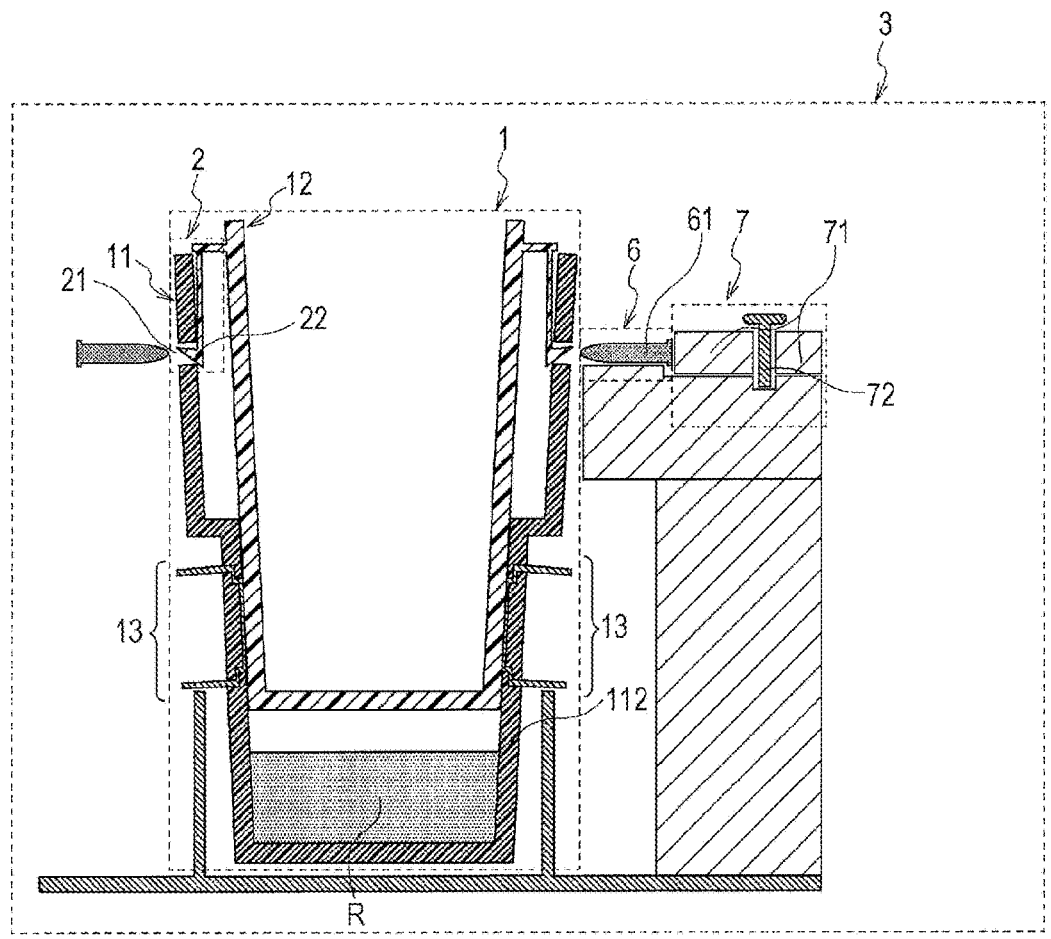

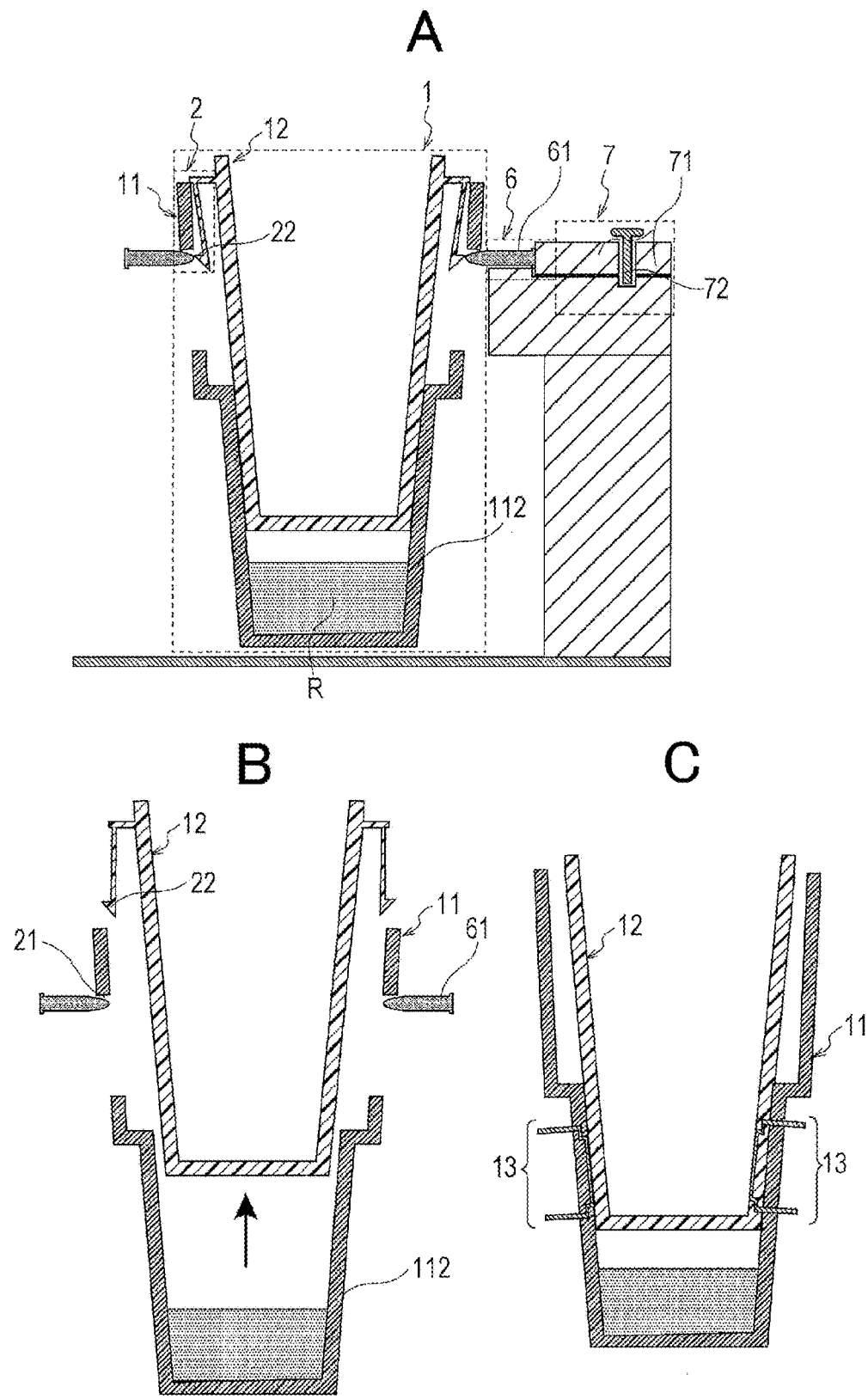
[Fig. 13]

[Fig. 14]
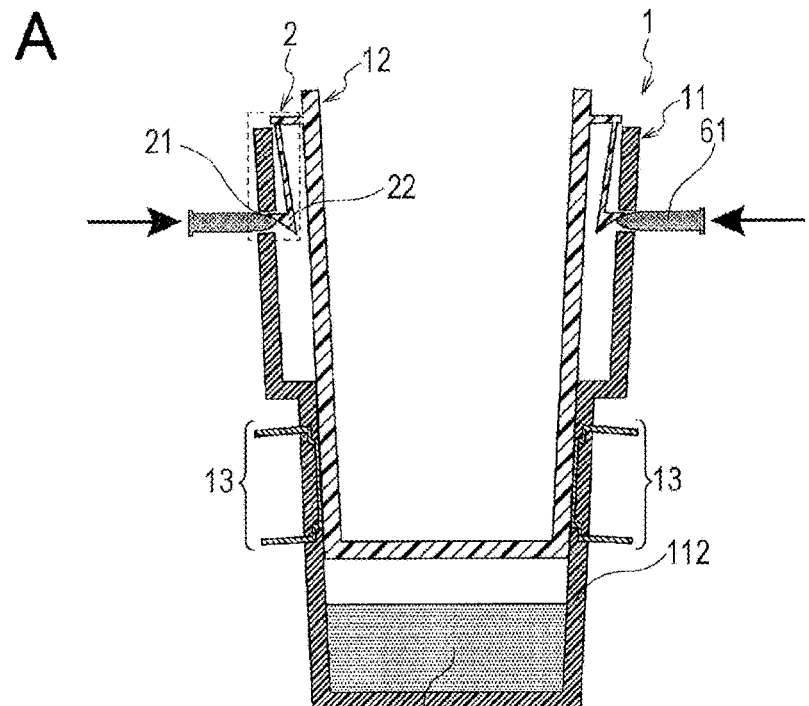
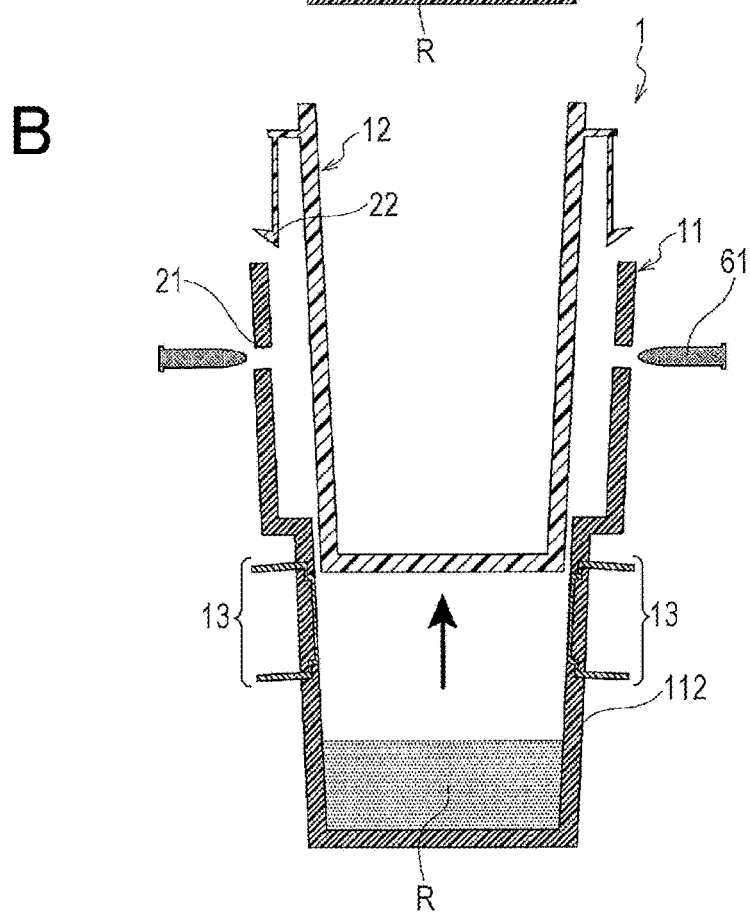

[Fig. 15]
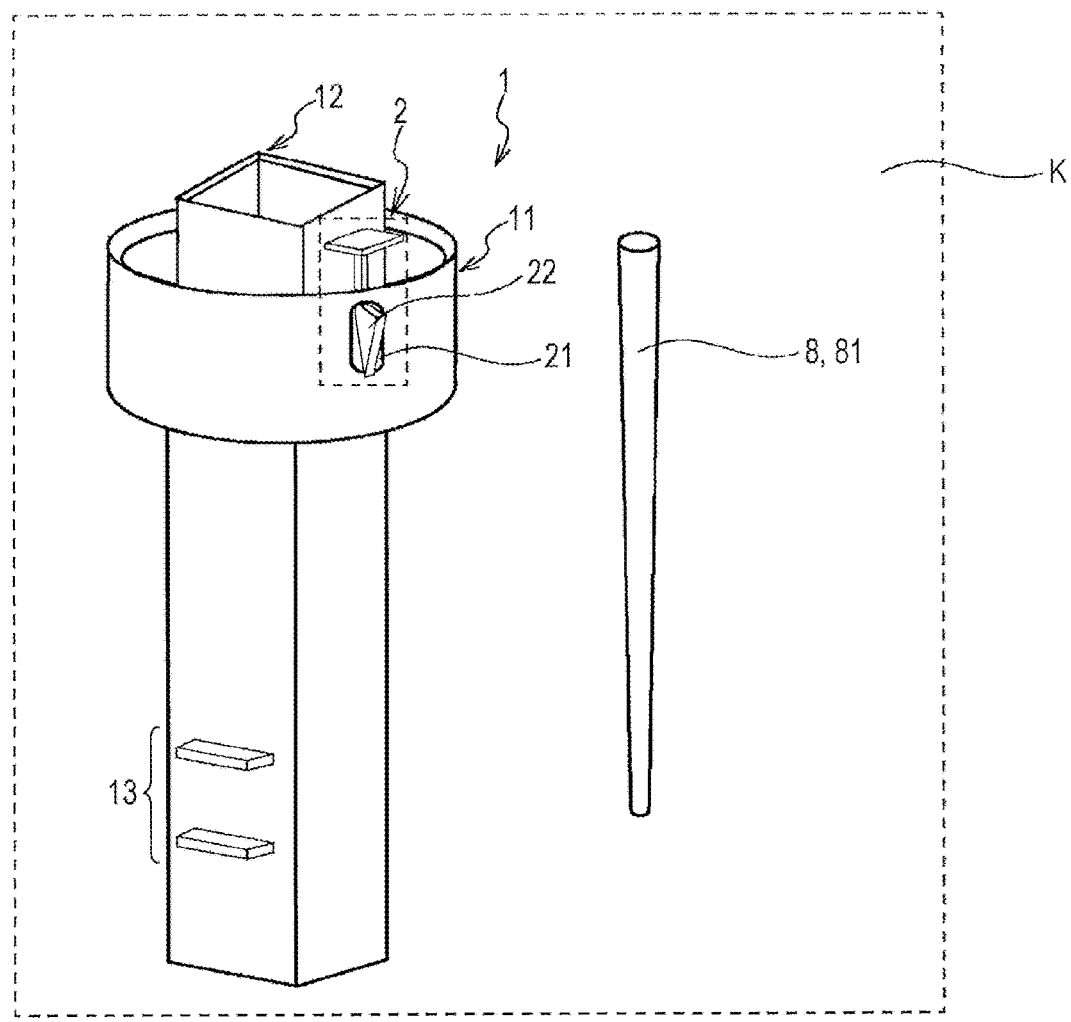

CARTRIDGE, KIT COMPRISING CARTRIDGE, ELECTRIC MEASURING APPARATUS, AND ELECTRIC MEASURING METHOD

CROSS REFERENCE TO RELATED APPLICATIONS

This application claims the benefit under 35 U.S.C. § 371 as a U.S. National Stage Entry of International Application No. PCT/JP2014/006487, filed in the Japanese Patent Office as a Receiving Office on Dec. 26, 2014, which claims priority to Japanese Patent Application JP 2014-233041 filed Nov. 17, 2014 and Japanese Patent Application JP 2014-001064 filed Jan. 7, 2014, each of which is hereby incorporated by reference in its entirety.

TECHNICAL FIELD

The present technology relates to a cartridge for electric measurement to measure electric characteristics of a sample. In particular, the present technology relates to a cartridge for electric measurement including a structure suitable for encapsulating a reagent used to measure electric characteristics of a sample and capable of improving the accuracy of measurement and an electric measuring apparatus and an electric measuring method using the cartridge for electric measurement.

BACKGROUND ART

Electric characteristics of a sample are measured to determine physical properties of the sample based on the measurement result or to determine the type of cells or the like contained in the sample (see, for example, PTL 1). Electric characteristics to be measured include the complex dielectric constant and the frequency dispersion (dielectric spectrum) thereof. The complex dielectric constant and the frequency dispersion thereof are generally calculated by measuring complex capacitance or complex impedance between electrodes by using a solution holder or the like including electrodes to apply a voltage to a solution.

In addition, for example, PTL 2 discloses a technology to acquire information about blood coagulation from the dielectric constant of blood and describes "a blood coagulation analyzer including a pair of electrodes, an application device for applying an alternating voltage to the pair of electrodes at predetermined intervals, a measuring device for measuring the dielectric constant of blood arranged between the pair of electrodes, and an analysis device for analyzing the degree of working of a blood coagulation system using the dielectric constant of the blood measured at the above intervals after the action of anticoagulant acting on the blood ceases".

As a container to contain a sample when measuring electric characteristics of the sample, for example, PTL 3 discloses a sample cartridge for measurement of electric characteristics of the sample formed from an insulating material in a cylindrical shape, capable of holding the sample in a region including the surface of an electrode inserted from an opening of each of both ends thereof and the surface of an inner space, and provided with a narrowed portion in which an inner space is narrowed positioned between two opposed electrodes in the region.

Incidentally, a reagent used for measurement of electric characteristics of a sample is generally encapsulated in a container in an ampoule-type or cap-type form.

The ampoule-type container needs to be melted and closed to encapsulate a reagent, leading to a heavy cost burden of equipment investment and the like. In addition, the user needs to cut a specific portion of the container when the container is unstopped, posing a problem of increased time and effort.

On the other hand, the cap-type container is available in two types, the screw type and the snap-in type. The screw type container poses a problem of an increased cost burden during manufacturing and increased time and effort when unstopped. The snap-in type container poses a problem of a flying reagent when unstopped.

In addition to the above containers, a combination of a simple cylindrical container and a cap (for example, an Eppendorf tube) poses a problem of a reagent in the container flying inside the container during transportation and remaining on the container wall, leading to lower accuracy of measurement.

Further, the reagent encapsulated in these containers needs to be distributively poured into each cartridge for measurement after unstopping when electric characteristics of a sample are measured. At this point, a problem of dust and the like in the air being mixed into the cartridge for measurement is posed.

CITATION LIST

Patent Literature

PTL 1: JP 2009-042141 A
PTL 2: JP 2010-181400 A
PTL 3: JP 2012-052906 A

SUMMARY

Technical Problem

As described above, a container in a conventional form has a problem of decreased convenience when unstopped or transported. Also when electric characteristics of a sample are measured, if measurement is attempted by using a reagent encapsulated in a conventional container, a problem of lower accuracy of measurement is posed for reasons of a more complicated measurement process and the like.

Thus, in the present technology, it is desirable to provide a cartridge for electric measurement including a structure suitable for encapsulating a reagent used to measure electric characteristics of a sample and capable of improving the accuracy of measurement.

Solution to Problem

To solve the above challenge, as a result of an intensive study on the structure of a cartridge, mainly used for measurement of electric characteristics of a sample, the inventors succeeded in solving the challenge by devising the physical relationship between a portion where a reagent is encapsulated and electrodes, resulting in successful completion of the present technology.

That is, according to the present technology, a cartridge comprising: a container comprising an opening and a holding portion to hold a sample and/or a reagent; an electrode disposed on a container wall of the container; and a removable separator to separate at least some of the holding portion of the container from the electrode when the removable separator is inserted into the holding portion, is provided.

The cartridge according to the present technology may be distributed in a kit, the kit further comprising a member to introduce the sample into the container. The member may be a pipet or may be an injection needle.

More specifically, according to the present technology, a kit comprises a cartridge comprising: a container comprising an opening and a holding portion to hold a sample and/or a reagent; an electrode, disposed on a container wall of the container with a part of the electrode extending to an interior surface of the container wall and to the holding portion, to apply an electrical signal to the sample and/or reagent as part of a diagnostic process; and a removable separator to separate at least some of the holding portion of the container from the electrode when the removable separator is inserted into the holding portion, and a member to introduce the sample into the container is provided.

Also, the cartridge for electric measurement according to the present technology may suitably be used as part of an electric measuring apparatus.

More specifically, in some embodiments there is provided an electric measuring apparatus comprising: a cartridge comprising: a container comprising an opening and a holding portion to hold a sample and/or a reagent; an electrode, disposed on a container wall of the container with a part of the electrode extending to an interior surface of the container wall and to the holding portion, to apply an electrical signal to the sample and/or reagent as part of a diagnostic process; and a removable separator to separate at least some of the holding portion of the container from the electrode when the removable separator is inserted into the holding portion, a cartridge holder into which the cartridge is inserted, a signal generating circuit to generate a first signal to be applied to the electrode of the cartridge, and a measuring circuit to measure at least one electric characteristic of a second signal, resulting from application of the first signal to the electrode of the cartridge, indicative of one or more electrical characteristics of the sample and/or the reagent disposed in the holding portion is provided.

Further, the cartridge may further comprise a clamp, the clamp comprising a notched portion provided in the container and a claw provided on the removable separator and arranged to catch in the notched portion when the removable separator is inserted into the holding portion, and the electric measuring apparatus may further comprising a sealing release member to, upon insertion of the cartridge into the cartridge holder, release the claw of the clamp from the notched portion.

Further, the cartridge for electric measurement according to the present technology can suitably be used for a method comprising removing a removable separator from a container of a cartridge, the cartridge comprising a reagent disposed in the container and an electrode at least partially disposed in the container, wherein prior to removal the removable separator formed a liquid-tight seal separating the reagent from the electrode; applying at least one electrical signal to the electrode of the cartridge; measuring at least one second signal resulting from application of the at least one electrical signal to the electrode of the cartridge; and determining at least one diagnostic result of a sample disposed with the reagent in the container based at least in part on the measuring.

Advantageous Effects of Invention

A cartridge for electric measurement according to the present technology has a structure in which at least a portion of a sample holding portion is sealed and so is suitable for encapsulating a reagent used for measurement of electric characteristics of a sample. The portion in which the reagent is encapsulated and an electrode are separated and therefore, the accuracy of measurement can be improved. The effects described here are not necessarily to be limited and may be any effect described in the present technology.

BRIEF DESCRIPTION OF DRAWINGS

FIG. 1A is a schematic end view schematically showing a first embodiment of a cartridge for electric measurement 1 according to the present technology, and FIG. 1B is a schematic end view in a state excluding a sealing portion from FIG. 1A;

FIG. 2A is a schematic end view schematically showing a second embodiment of the cartridge for electric measurement 1 according to the present technology, FIG. 2B is an L-L' arrow end view of FIG. 2A, and FIG. 2C is an M-M' arrow end view of FIG. 2A;

FIG. 3 is a schematic end view schematically showing a third embodiment of the cartridge for electric measurement 1 according to the present technology;

FIG. 4A is a schematic end view schematically showing a fourth embodiment of the cartridge for electric measurement 1 according to the present technology, and FIG. 4B is a schematic end view in a state excluding the sealing portion from FIG. 4A. Further, FIG. 4C is an L-L' arrow end view of FIG. 4A and FIG. 4D is an M-M' arrow end view of FIG. 4A;

FIG. 5 is a schematic end view schematically showing a fifth embodiment of the cartridge for electric measurement 1 according to the present technology;

FIG. 6 is a schematic end view schematically showing a sixth embodiment of the cartridge for electric measurement 1 according to the present technology;

FIG. 7A is a schematic end view schematically showing a seventh embodiment of the cartridge for electric measurement 1 according to the present technology, and FIGS. 7B and 7C are enlarged views of a broken line portion in FIG. 7A;

FIG. 8 is a schematic end view schematically showing an eighth embodiment of the cartridge for electric measurement 1 according to the present technology;

FIG. 9 is a schematic end view schematically showing a ninth embodiment of the cartridge for electric measurement 1 according to the present technology;

FIG. 10A is a schematic view schematically showing a tenth embodiment of the cartridge for electric measurement 1 according to the present technology, FIG. 10B is an arrow end view when viewed from an L side in FIG. 10A, and FIG. 10C is an arrow end view when viewed from an M side in FIG. 10A;

FIG. 11 is a schematic diagram schematically showing the first embodiment of an electric measuring apparatus 10 according to the present technology;

FIG. 12 is a schematic end view schematically showing a detailed example of an eleventh embodiment of the cartridge for electric measurement 1 according to the present technology and a cartridge insertion portion 3 of the electric measuring apparatus 10 according to the present technology;

FIG. 13A is a schematic end view schematically showing an example of an instant when a sealed state of a sample holding portion 112 is released by a release pin 61 in the cartridge for electric measurement 1 (twelfth embodiment) according to the present technology. FIG. 13B is a schematic end view schematically showing an example immediately after the sealed state being released by the release pin 61;

FIG. 13C is a schematic end view schematically showing the cartridge for electric measurement 1 (twelfth embodiment) viewed from a direction perpendicular to the sectional view in FIG. 13A;

FIG. 14A is a schematic end view schematically showing an example that is different from the example in FIG. 13 of the instant when the sealed state of the sample holding portion 112 is released by the release pin 61 in the cartridge for electric measurement 1 (eleventh embodiment) according to the present technology. FIG. 14B is a schematic end view schematically showing an example that is different from the example in FIG. 13 immediately after the sealed state being released by the release pin 61; and FIG. 15 is a schematic diagram schematically showing the first embodiment of a kit for electric measurement K according to the present technology.

DESCRIPTION OF EMBODIMENTS

Preferred embodiments to carry out the present technology will be described below with reference to the drawings. The embodiments described below show some representative embodiments of the present technology and the scope of the present technology will not be thereby interpreted in a narrow sense. The description will be provided in the order shown below:
1. Cartridge for electric measurement 1
   (1) Container 11
   (a) Opening 111
   (b) Sample holding portion 112
   (2) Sealing portion 12
   (3) Electrode 13
   (4) Clamping mechanism 2
   (a) Notched portion 21
   (b) Claw 22
   (5) Sample S
   (6) Reagent R
   (7) Others
2. Electric measuring apparatus 10
   (1) Cartridge insertion portion 3
   (2) Application unit 4
   (3) Measuring unit 5
   (4) Sealing release mechanism 6
   (5) Others
3. Kit for electric measurement K
   (1) Member for sample introduction 8
4. Electric measuring method 1. Cartridge for Electric Measurement 1

FIG. 1A is a schematic end view schematically showing the first embodiment of the cartridge for electric measurement 1 according to the present technology. The cartridge for electric measurement 1 according to the present technology is a cartridge used to hold a sample when electric characteristics of the sample are measured. The cartridge for electric measurement 1 according to the present technology roughly includes at least a container 11, a sealing portion 12, and an electrode 13. In addition, as will be described later, a clamping mechanism 2 or the like may be included if necessary. Each portion (unit) will be described in detail below. Though a sample S and/or a reagent R is illustrated in each drawing from a description viewpoint, the sample S and/or the reagent R is not necessarily included in the cartridge for electric measurement 1 according to the present technology.

(1) Container 11

In the cartridge for electric measurement 1 according to the present technology, the container 11 enables the introduction/holding of the sample S and/or the reagent R. The container 11 according to the present technology is characterized in that at least an opening 111 and a sample holding portion 112 are included.

In the cartridge for electric measurement 1 according to the present technology, the form of the container 11 is not particularly limited and can freely be designed in accordance with the type of the sample S or the reagent R, the measuring method, or the measuring apparatus to be used. The form may be, for example, a cylindrical body, a polygonal cylinder whose cross section is polygonal (triangular, quadrangular or more), a conical body, a polygonal cone whose cross section is polygonal (triangular, quadrangular or more), or a combination of two or more of these forms.

In the present technology, particularly in the container 11, it is preferable to select a form in which at least a portion where the electrode 13 is arranged is a flat surface. As a more concrete example, for example, a form combining, like the second embodiment shown in FIG. 2, a cylindrical body and a quadrangular cylinder whose cross section is quadrangular can be cited. In general, the electrode used for measurement of electric characteristics has frequently a plane or plate shape. If a cylindrical shape is selected for the container 11 according to the present technology, the electrode 13 in a plane or plate shape will be mounted on a curved portion, which makes the manufacturing process very complex. In addition, if the electrode 13 in a plane or plate shape is mounted on a curved portion of the container 11, a step is likely to arise in a connection portion of the container 11 and the electrode 13 and, as will be described later, the efficiency of measurement may deteriorate during measurement of electric characteristics. Therefore, by selecting a form of the container 11 in which at least a portion where the electrode 13 is arranged is plane, simplification of the manufacturing process and improvements of the efficiency of measurement can be realized.

The container 11 according to the present technology may have, like the third embodiment shown in FIG. 3, a gradient from a container bottom 113 toward the opening 111 on at least a portion of an inner wall side if necessary. The angle of gradient is not particularly limited, but as will be described later, if the container 11 is formed by using resin, it is preferable to have an angle of 1 degree or more.

(a) Opening 111

The opening 111 is a site through which the sample S and/or the reagent R to be measured can be introduced.

(b) Sample Holding Portion 112

The sample holding portion 112 is a site by which the sample S and/or the reagent R to be measured can be held. Various electric characteristics are measured while the sample S being held by the sample holding portion 112.

In addition, as will be described later, the sample holding portion 112 according to the present technology is characterized in that at least a portion thereof is sealed by the sealing portion 12 and the electrode 13 is fixed.

The method of concretely introducing the sample S and/or the reagent R into the sample holding portion 112 is not particularly limited and the method can freely be selected for introduction in accordance with the form of the container 11.

To introduce the sample S, for example, the sealing portion 12 is removed from the cartridge for electric measurement 1 to create a state as shown in FIG. 1B and then, the sample S is introduced into the sample holding portion 112 using a pipet or the like. When the sample S is introduced, the reagent R can also be introduced and the sample S may also be introduced to a place where the reagent R is encapsulated in the sample holding portion 112 in advance.

To introduce the reagent R, for example, the sealing portion 12 is removed from the cartridge for electric measurement 1 to create a state as shown in FIG. 1B and then, the reagent R is introduced into the sample holding portion 112 using a pipet or the like. In this case, the sealing portion 12 once removed can be fitted into the container 11 again to encapsulate the reagent R in a sealed portion of the sample holding portion 112. In a state as shown in FIG. 1A in which the sealing portion 12 is present, a method of introducing the reagent R by putting an injection needle from an outer wall of the sample holding portion 112 and after the reagent R is injected, filling a portion through the injection needle is passed with grease or the like can be considered. In this case, the sealing portion 12 remained fitted into the container 11.

As described above, the cartridge for electric measurement 1 according to the present technology can encapsulate the reagent R in a sealed portion of the sample holding portion 112. Thus, the cartridge for electric measurement 1 according to the present technology can be transported or stored while the reagent R is encapsulated in the sample holding portion 112 of the cartridge for electric measurement 1 in advance.

When electric characteristics are measured, the cartridge for electric measurement 1 holds the sample S in the sample holding portion 112 and the sealing portion 12 is removed therefrom (see FIG. 1B).

(2) Sealing Portion 12

In the cartridge for electric measurement 1 according to the present technology, the sealing portion 12 is characterized in that at least a portion of the sample holding portion 112 is sealed and also the sealed portion and the electrode 13 are separated.

In the cartridge for electric measurement 1 according to the present technology, measurements are started after the sealing portion 12 being removed before the start of measurement of the electric characteristics. Thus, the attachment of dust in the air that could cause deterioration of the accuracy of measurement to the electrode 13 or entrapment thereof into the sample holding portion 112 can be avoided. Also in the cartridge for electric measurement 1 according to the present technology, the sample holding portion 112 and the electrode 13 are separated by the sealing portion 12 and thus, for example, when the cartridge is stored or transported while the reagent R is encapsulated in the sample holding portion 112 in advance, the reagent R can be prevented from flying to the inner wall near the opening 111 or the electrode 13. Therefore, the effective amount of reagent for the sample S can be maintained.

Also, if the reagent R is, for example, a liquid, a chemical reaction with the electrode 13 may occur or the electrode 13 may be corroded after the reagent R being attached to the electrode 13, but in the cartridge for electric measurement 1 according to the present technology, the sample holding portion 112 and the electrode 13 are separated by the sealing portion 12; therefore, a chemical reaction with and corrosion of the electrode 13 due to attachment of the reagent R to the electrode 13 can be prevented. Further, for example, in the electrode 13 portion, a reaction (for example, a blood-clotting reaction) of the sample S (for example, an organism sample such as a blood sample) occurs in some cases more easily under the influence of metal ions; therefore, measurement errors due to a heterogeneous reaction caused by a liquid reagent R or a freeze-dried reagent R attached to the electrode 13 can be reduced.

In the cartridge for electric measurement 1 according to the present technology, the form of the sealing portion 12 is not particularly limited and can freely be designed in accordance with the type of the sample S or the reagent R, the measuring method, or the measuring apparatus to be used. The form may be, for example, a cylindrical body, a polygonal cylinder whose cross section is polygonal (triangular, quadrangular or more), a conical body, a polygonal cone whose cross section is polygonal (triangular, quadrangular or more), or a combination of two or more of these forms. As a more concrete example, for example, a form combining, like the fourth embodiment shown in FIG. 4, two cylindrical bodies and a quadrangular cylinder whose cross section is quadrangular can be cited.

If the sealing portion 12 has the form of, for example, the first embodiment in FIG. 1 or the second embodiment in FIG. 2, when inserted into the container 11, the sealing portion initially reduces the amount of content while sliding along the inner wall of the container 11 and reaches a critical point in the end by covering an exposed portion of the electrode 13 fixed to the sample holding portion 112. The critical point can freely be designed depending on the degree of fitting between the container 11 and the sealing portion 12.

Further, the sealing portion 12 may have, like the fifth embodiment shown in FIG. 5, a gradient spreading from a bottom 121 of the sealing portion to an upper portion 122 of the sealing portion on at least a portion of the outer wall if necessary. The angle of gradient is not particularly limited, but as will be described later, if the sealing portion 12 is formed by using resin, it is preferable to have an angle of 1 degree or more.

In addition, the sealing portion 12 may be designed so as to be subject to a stress in a sealing release direction from the container 11. The structure to be subject to a stress is not particularly limited and, for example, like the sixth embodiment shown in FIG. 6, a structure in which a gradient spreading from the bottom to the opening 111 is formed on at least a portion of the inner wall of the container 11 and at least a portion of the outer wall of the sealing portion 12 and the gradient on the outer wall of the sealing portion 12 is designed to be equivalent to the gradient on the inner wall of the container 11 or more can be cited. By designing the gradient on the outer wall of the sealing portion 12 to be equivalent to the gradient on the inner wall of the container 11 or more, the sealing portion 12 becomes subject to a stress in the sealing release direction from the container 11. As a result, the sealing portion 12 can be removed more easily from the container 11 for electric measurements or the like.

The material used for the container 11 and the sealing portion 12 constituting the cartridge for electric measurement 1 according to the present technology is not particularly limited and in the present technology, the container 11 and the sealing portion 12 can be formed by using resin.

The type of resin that can be used for the cartridge for electric measurement 1 according to the present technology is not particularly limited and one or two resins or more applicable for holding the sample can freely be selected and used. For example, hydrophobic and insulating polymers, copolymers, or blend polymers of polypropylene, polymethyl methacrylate, polystyrene, acrylic, polysulfone, polytetrafluoroethylene and the like can be cited. In the present technology, the container 11 and the sealing portion 12 are preferably formed from resin selected from, among others, particularly polypropylene, polystyrene, acrylic, and polysulfone. These resins have low coagulation activity to blood and so can also be suitably used, for example, to measure a biological sample containing blood.

FIG. 7A is a schematic end view schematically showing the seventh embodiment of the cartridge for electric measurement 1 according to the present technology. The sealing portion 12 according to the present technology may be provided with a through hole 123 that is opened (see FIG. 7B) when the sample holding portion 112 as shown in the seventh embodiment is in a non-sealed state and closed (see FIG. 7C) when at least a portion of the sample holding portion 112 is in a sealed state. More specifically, the through hole 123 is open when the sealing portion 12 is separated from the container 11 and is gradually closed by an external force when the sealing portion 12 is inserted into the container 11 before being completely closed when the sealing portion 12 reaches a limiting point in the end.

By providing the through hole 123, the through hole 123 becomes a byway of air encapsulated in a sealed portion of the sample holding portion 112 when the sealing portion 12 is inserted into the container 11. Therefore, when the sealing portion 12 is slid into the container 11, the resistance due to air pressure falls. As a result, the convenience of the user is improved by the ease with which the sealing portion 12 is inserted into the container 11.

Though not illustrated, the form of the bottom 121 of the sealing portion can be formed in a convex shape toward the upper portion 122 of the sealing portion. By adopting a convex shape as the form of the bottom 121 of the sealing portion, the bottom 121 of the sealing portion is made more flexible. As a result, the convenience of the user is improved by the ease with which the sealing portion 12 is inserted into the container 11.

Further, the sealing portion 12 according to the present technology may be provided with packing 124 as shown in the eighth embodiment shown in FIG. 8 at the bottom 121 of the sealing portion. By providing the packing 124, a contact area between the outer wall of the sealing portion 12 and the inner wall of the container 11 decreases when the sealing portion 12 is slid into the container 11, reducing friction. As a result, the convenience of the user is improved by the ease with which the sealing portion 12 is inserted into the container 11.

The sealing portion 12 and the packing 124 may be formed by using different materials. When different materials are formed, the packing 124 and the sealing portion 12 can integrally be formed by the method of two-color molding or the like.

The material used for the packing 124 is not particularly limited and in the present technology, an elastic material is preferably used. Elastic materials include, in addition to a silicone elastomer of polydimethylsiloxane (PDMS) and the like, an acrylic elastomer, a urethane elastomer, a fluorine elastomer, a styrene elastomer, an epoxy elastomer, and natural rubber. By using an elastic material for the packing 124, a sealed state of the sample holding portion 112 is more likely to be formed.

(3) Electrode 13

In the cartridge for electric measurement 1 according to the present technology, the electrode 13 is characterized by being fixed to the sample holding portion 112 in advance. The electrode 13 according to the present technology is used to come into contact with the sample S for electric measurement to apply a necessary voltage to the sample S.

In the present technology, the method of fixing the electrode 13 to the sample holding portion 112 is not particularly limited, but it is preferable to integrally form the sample holding portion 112 and the electrode 13 while a portion of the electrode 13 is buried in the sample holding portion 112. By integrally forming the sample holding portion 112 and the electrode 13, an adverse effect on the sample S or the reagent R held by the sample holding portion 112 can be excluded.

When, for example, the electrode 13 is fixed to the sample holding portion 112 by using an adhesive, properties of the sample S or the reagent R may adversely be affected depending on the adhesive to be used. When, for example, electric characteristics of blood are measured as the sample S, coagulation activity of blood may be promoted depending on the adhesive to be used, adversely affecting intended measurements. However, by adopting the method of integrally forming the sample holding portion 112 and the electrode 13, that is, the method that does not use a fixing material such as an adhesive to fix the sample holding portion 112 and the electrode 13, an adverse effect of the fixing material such as an adhesive on the sample S or the reagent R can be excluded. As a result, improvements of the accuracy of measurement during electric measurement are realized.

Even if a fixing material affecting the sample S or the reagent R only slightly is used, the adhesion process by the fixing material increases when cartridges for accommodating a sample are manufactured, posing a problem of reduced productivity. However, by adopting the method of integrally forming the sample holding portion 112 and the electrode 13, there is no need to separately provide the adhesion process, in addition to the molding process of the sample holding portion 112. As a result, the manufacture of the cartridge for electric measurement 1 is made easier and therefore, the cartridge for electric measurement 1 can be mass-produced at low prices.

In addition, there is a method of measuring electric characteristics while an electrode is inserted from outside into a cartridge accommodating a sample. According to this method, however, a problem of measurement errors arising due to a difference of the insertion amount of the electrode in the sample is posed. In the cartridge for electric measurement 1 according to the present technology, however, the electrode 13 is fixed to the sample holding portion 112 in advance and measurement errors due to a difference of the insertion amount of the electrode in the sample can be eliminated. As a result, the accuracy of measurement during electric measurement can be improved.

In addition, with the electrode 13 being fixed to the sample holding portion 112 in advance, there is no need to install a relative positioning mechanism relative to the cartridge accommodating an electrode and a sample on the device side so that the configuration on the device side can also be simplified. As a result, a contribution can be made to realize miniaturization of devices, simplification of manufacturing processes, and lower prices of devices.

The concrete method of integrally forming the sample holding portion 112 and the electrode 13 is not particularly limited and a free method can be used. For example, the container 11 and the electrode 13 can integrally be formed by arranging the electrode 13 in a predetermined position when the resin forming the container 11 is set up from a molten state. As a more concrete method, for example, the container 11 and the electrode 13 can integrally be formed by so-called insert molding in which the electrode 13 is inserted into a die and injecting a resin therearound to integrate the electrode 13 and the resin.

Thus, the manufacturing processes can be simplified by, when the container 11 is formed, fixing the electrode 13 at the same time. As a result, the cartridge for electric measurement 1 according to the present technology can be mass-produced at low prices.

The electrode 13 is formed from an electrically conductive material. In the cartridge for electric measurement 1 according to the present technology, the type of electrically conductive material used for the electrode 13 is not particularly limited and one or two materials or more applicable for electric measurement of the sample S can freely be selected and used. For example, titanium, aluminum, stainless, platinum, gold, copper, and graphite can be cited. In the present technology, among others, it is preferable to form the electrode 13 from an electrically conductive material particularly containing titanium. Titanium has low coagulation activity to blood and so can also be suitably used, for example, to measure a biological sample containing blood.

Also in the cartridge for electric measurement 1 according to the present technology, the number of the electrodes 13 can freely be designed in accordance with the method of intended electric measurements. When, for example, the dielectric constant or impedance of the sample S is measured, a pair of the electrodes 13 or more can be provided.

Further, the arrangement and form of the electrode 13 are not particularly limited and can freely be designed in accordance with the form of the sample holding portion 112 or the intended electric measuring method as long as a necessary voltage can be applied to the sample S, but in the present technology, as shown in the sixth embodiment in FIG. 6, the connection portion between the sample holding portion 112 and the electrode 13 is preferably in contact with the sample S in a plane particularly to improve the efficiency of measurement. This is because if, for example, as shown in the fourth embodiment in FIG. 4, there is a step on the inner wall of the sample holding portion 112, air bubbles may remain in a step portion (see a broken line portion X in FIG. 4B) or unevenness of the reagent concentration may arise in the step portion, adversely affecting measured values. Therefore, by integrally forming the sample holding portion 112 and the electrode 13 such that the connection portion therebetween is smooth like in the sixth embodiment, the accuracy of measurement when electric characteristics are measured can be improved by excluding adverse effects such as air bubbles and unevenness of sample concentrations.

When a pair or more of the electrodes 13 are included, it is preferable to arrange each of the electrodes 13 in parallel from the viewpoint of measuring electric characteristics of the sample S. However, in consideration of, for example, mold release characteristics when insert molding is performed, as shown in the sixth embodiment in FIG. 6, each of the electrodes 13 can be arranged in a state of a few degrees of gradient.

Though very rare, the sample S or the reagent R may leak out from a border between the sample holding portion 112 and the electrode 13 depending on storage conditions such as the temperature or measuring conditions due to a difference of strain between resin and an electrically conductive material or the like. Thus, in the electrode 13 according to the present technology, like the seventh embodiment shown in FIG. 7A, by including a curved portion in a portion of the structure fixed to the sample holding portion 112, when compared with the sixth embodiment in FIG. 6 including no curved portion, the sample S or the reagent R can reliably be prevented from leaking out from the border between the sample holding portion 112 and the electrode 13.

Also, by including a curved portion in the electrode 13, fixing of the sample holding portion 112 and the electrode 13 is made firmer and the robust cartridge for electric measurement 1 can be formed.

Further, the cartridge for electric measurement 1 according to the present technology can be configured, like the seventh embodiment in FIG. 7A, not to include resin in a cartridge outer portion of the pair of electrodes 13. By adopting such a configuration, when, for example, the sample holding portion 112 is formed, the electrode 13 can be positioned in a desired position of the cartridge for electric measurement 1 by positioning and fixing the electrode 13 by using, for example, a magnetic means such as a magnet. However, a fixing means of the electrode 13 from outside the cartridge is not limited to the above magnetic means and any means capable of fixing the electrode 13 from outside the cartridge can be used.

Thus, by causing at least a portion of the electrode 13 as a holding portion to arrange the sample holding portion 112 in a predetermined position during integral formation, the cartridge for electric measurement 1 in which the electrode 13 is correctly positioned in a predetermined position can easily be manufactured.

By the electrode 13 being held during formation of the sample holding portion 112, the electrode 13 can be prevented from being deformed during integral formation.

(4) Clamping Mechanism 2

The cartridge for electric measurement 1 according to the present technology can further include the clamping mechanism 2. In the present technology, more specifically, the clamping mechanism 2 is a mechanism that fixes the container 11 and the sealing portion 12 when the sealing portion 12 seals at least a portion of the sample holding portion 112. The clamping mechanism 2 is not particularly limited, but can be configured by, for example, like the ninth embodiment shown in FIG. 9, a notched portion 21 provided in the container 11 and a claw 22 fitted into the notched portion 21 and provided in the sealing portion 12. With the clamping mechanism 2 being included in the cartridge for electric measurement 1, the sealing portion 12 can be prevented from being detached from the container 11. As a result, a sealed state of the sample holding portion 112 and the sealing portion 12 can be maintained in a stable manner.

The clamping mechanism 2 can also be designed such that re-fixing is difficult to achieve after fixing is released. With the clamping mechanism being made incapable of re-fixing after fixing is released, the cartridge for electric measurement 1 once unstopped is made incapable of fitting the container 11 and the sealing portion 12. As a result, a history of unstopping the cartridge for electric measurement 1 can be checked. When, for example, the cartridge for electric measurement 1 is distributed with the reagent R encapsulated, the quality thereof can be guaranteed.

(a) Notched Portion 21

In the cartridge for electric measurement 1 according to the present technology, the notched portion 21 is characterized by being provided in the container 11 and structured to be able to fit into the claw 22. The form of the notched portion 21 is not particularly limited and, for example, a hole, a groove or the like provided in the container 11 can be cited. More specifically, for example, a hole provided so as to pass through from the inner wall to the outer wall of the container 11 can be cited.

(b) Claw 22

In the cartridge for electric measurement 1 according to the present technology, the claw 22 is characterized by being provided in the sealing portion 12 and structured to be able to fit into the notched portion 21. The form of the claw 22 is not particularly limited and, for example, a projection or the like provided in the sealing portion 12 can be cited.

The claw 22 can also be designed to be flexible. For example, the method of forming the claw 22 from a flexible material such as a resin can be cited. With the claw 22 being flexible, fitting into the notched portion 21 becomes easier and, as a result, the convenience of the user is improved.

FIG. 10A is a schematic view schematically showing the tenth embodiment of the cartridge for electric measurement 1 according to the present technology, FIG. 10B is an arrow end view when viewed from the L side in FIG. 10A, and FIG. 10C is an arrow end view when viewed from the M side in FIG. 10A. In the tenth embodiment, the claw 22 is configured to have play with respect to the outer wall of the sealing portion 12 by designing the claw 22 so as not to directly come into contact with the outer wall of the sealing portion 12. By configuring the claw 22 to have play with respect to the outer wall of the sealing portion 12 as described above, the ease with which the claw is fitted into the notched portion 21 can be improved.

In the tenth embodiment shown in FIG. 10, the electrode 13 and the clamping mechanism 2 are arranged on different side faces of the container 11. By arranging the electrode 13 and the clamping mechanism 2 on different side faces of the container 11, contact with a sealing release mechanism 6 (see FIG. 13 described later) of the electrode 13 when the cartridge 1 is inserted into a cartridge insertion portion 3 of the electric measuring apparatus 10 described later can be prevented.

The claw 22 may also be designed to be deformable or cuttable to make re-fixing difficult to achieve when fixing of the clamping mechanism 2 is released. The mechanism to deform or cut the claw 22 is not particularly limited and, for example, a method of melting and deforming the claw 22 by a chemical means using heat or the like and a method of cutting the claw 22 by a physical means can be cited. With the claw 22 deformed or cut, it becomes difficult to re-fit the claw 22 and the notched portion 21. Therefore, fitting the container 11 and the sealing portion 12 also becomes difficult to achieve so that the quality of the cartridge for electric measurement 1 can be guaranteed.

In the cartridge for electric measurement 1 according to the present technology, like the container 11 and the sealing portion 12, resin can also be used for the notched portion 21 and the claw 22. The type of resin is as described above and the description thereof is omitted here.

(5) Sample S

The sample S that can be measured by the present technology is not particularly limited and can freely be selected. For example, a biological sample can be cited as the sample S. More specifically, a biological sample containing blood components such as whole blood, plasma, or a diluent thereof and/or drug additives can be cited.

(6) Reagent R

The reagent R that can be held by the sample holding portion 112 is not particularly limited in the present technology and can freely be selected. For example, a gaseous, solid, or liquid reagent can be cited as the reagent R.

The cartridge for electric measurement 1 according to the present technology is particularly suitable for a liquid reagent. Because the reagent R can be encapsulated in a sealed portion of the sample holding portion 112, the cartridge for electric measurement 1 is useful for a liquid reagent with fly properties during transportation. Also in the cartridge for electric measurement 1 according to the present technology, the sample holding portion 112 and the electrode 13 are separated by the sealing portion 12 and thus, the liquid reagent R can be prevented from flying to the inner wall near the opening 111 of the container 11 or the electrode 13. Therefore, the effective amount of reagent for the sample S can be maintained and also measurement errors due to the reagent R remaining on the electrode 13 can be reduced when electric characteristics are measured.

When a biological sample containing blood components is to be measured, an anticoagulant, a coagulation initiator and the like can be cited as the liquid reagent.

The cartridge for electric measurement 1 according to the present technology can be transported or stored while the reagent R is encapsulated in the sample holding portion 112 of the cartridge for electric measurement 1 in advance. In this case, the measurement can be started only after a process of unstopping the cartridge for electric measurement 1 and introducing the sample S to be measured into the sample holding portion 112 immediately before measuring electric characteristics. Thus, the entrapment of dust in the air that could cause deterioration of the accuracy of measurement into the sample holding portion 112 can be avoided. As a result, improvements of the accuracy of measurement are realized. Further, increasing complication of the measuring process is prevented by reduced work processes before starting the measurement and also the convenience of the user is improved.

The cartridge for electric measurement 1 according to the present technology can also be stored by the method of refrigeration, freezing, or freeze-drying while the reagent R is encapsulated depending on the type of reagent used as the reagent R.

(7) Others

As described above, the cartridge for electric measurement 1 according to the present technology can be mass-produced at low prices. Using the above features, for example, the cartridge for electric measurement 1 according to the present technology can be made a single-use cartridge. By making the cartridge for electric measurement 1 according to the present technology a single-use cartridge, time and effort to clean the cartridge can be saved and measurements can be made more efficient. In addition, an occurrence of measurement errors due to another sample S remaining in the container can be prevented so that the accuracy of measurement can be improved.

2. Electric Measuring Apparatus 10

FIG. 11 is a schematic diagram schematically showing the first embodiment of the electric measuring apparatus 10 according to the present technology. In the present embodiment, the cartridge for electric measurement 1 according to the aforementioned sixth embodiment is used. The electric measuring apparatus 10 according to the present technology roughly includes at least the cartridge for electric measurement 1, the cartridge insertion portion 3, an application unit 4, and a measuring unit 5. In addition, as will be described later, the sealing release mechanism 6 that releases a sealed state of at least a portion of the sample holding portion 112 or a mechanism to position the cartridge for electric measurement 1 according to the present technology may be included if necessary. Each portion (unit) will be described in detail below. The cartridge for electric measurement 1 is as described above and the description thereof is omitted here.

(1) Cartridge Insertion Portion 3

FIG. 12 is a schematic end view schematically showing a detailed example of the eleventh embodiment of the cartridge for electric measurement 1 according to the present technology and the cartridge insertion portion 3 of the electric measuring apparatus 10 according to the present technology. The cartridge for electric measurement 1 according to the present technology is inserted into the cartridge insertion portion 3 according to the present technology. The cartridge insertion portion 3 can freely be designed by fitting to the form of the cartridge for electric measurement 1.

The cartridge insertion portion 3 may include a temperature control mechanism. The temperature control mechanism is concretely a mechanism that enables the sample S and/or the reagent R held by the sample holding portion 112 to be kept at a constant temperature. More specifically, for example, by forming the cartridge insertion portion 3 from a material capable of insulating heat, the cartridge for electric measurement 1 according to the present technology is designed to keep the sample S and/or the reagent R at a constant temperature while the cartridge for electric measurement is inserted into the electric measuring apparatus 10.

(2) Application Unit 4

The application unit 4 applies a voltage to the electrode 13 of the cartridge for electric measurement 1 according to the present technology. The application unit 4 applies a voltage to the electrode 13 of the cartridge for electric measurement 1 when an instruction to start measurement is received or the power of the electric measuring apparatus 10 is turned on as the start point. More specifically, the application unit 4 applies an AC voltage of a predetermined frequency to the electrode 13 at set measuring intervals. The voltage applied by the application unit 4 may be a DC voltage in accordance with electric characteristics to be measured.

(3) Measuring Unit 5

The measuring unit 5 measures electric characteristics of the sample S held by the cartridge for electric measurement 1 according to the present technology. More specifically, electric characteristics such as the complex dielectric constant (hereinafter, called simply as a "dielectric constant") and the frequency dispersion thereof are measured when an instruction to start measurement is received or the power of the electric measuring apparatus 10 is turned on as the start point. More specifically, for example, when the dielectric constant is measured, the measuring unit 5 measures the current or impedance between the electrodes 13 of the cartridge for electric measurement 1 at predetermined intervals and derives the dielectric constant from the measured values. For the derivation of the dielectric constant, a known function or formula showing a relationship between the current or impedance and the dielectric constant can be used.

(4) Sealing Release Mechanism 6

The electric measuring apparatus 10 according to the present technology can also include the sealing release mechanism 6. In the present technology, the sealing release mechanism 6 is concretely a mechanism that releases at least a portion of a sealed state of the sample holding portion 112. The sealing release mechanism 6 is not particularly limited and can be embodied by, when, for example, the cartridge for electric measurement 1 includes the clamping mechanism 2, releasing fixing of the container 11 and the sealing portion 12 by the clamping mechanism 2 by using a chemical mechanism using heat or a physical mechanism.

More specifically, as shown, for example, in the eleventh embodiment in FIG. 12, a method of arranging the release pin 61 on the side of the electric measuring apparatus 10 when the cartridge for electric measurement 1 is inserted into the cartridge insertion portion 3 can be considered.

A concrete example of releasing fixing of the container 11 and the sealing portion 12 by the clamping mechanism 2 by using the release pin 61 will be described. The release pin 61 is installed in a position so that when, for example, the cartridge for electric measurement 1 is inserted into the cartridge insertion portion 3, as shown in FIG. 13, the cartridge comes into contact with the claw 22 provided in the sealing portion 12. If, in this state, the cartridge for electric measurement 1 is inserted into the cartridge insertion portion 3 and the claw 22 provided in the sealing portion 12 is brought into contact with the release pin 61, the claw 22 is pushed and deformed by the release pin 61. Fitting of the sealing portion 12 and the notched portion 21 provided in the container 11 is released by the deformation of the claw 22 and, as shown in FIG. 13B, a stress is generated in the arrow direction in FIG. 13B with respect to the sealing portion 12. As a result, only the sealing portion 12 moves in a detachment direction so that the cartridge for electric measurement 1 can be inserted into the cartridge insertion portion 3 and at the same time, only the sealing portion 12 can smoothly be removed from the container 11. FIG. 13C is a schematic end view schematically showing the cartridge for electric measurement 1 (twelfth embodiment) viewed from a direction perpendicular to the sectional view in FIG. 13A. In the present embodiment, from the viewpoint of preventing deformation, breakage and the like caused by contact of the electrode 13 with the release pin 61, like the tenth embodiment described above, the electrode 13 and the clamping mechanism 2 are arranged on different side faces of the container 11.

As another release example, when, for example, the cartridge for electric measurement 1 is inserted into the cartridge insertion portion 3, as shown in FIG. 14A, the claw 22 provided in the sealing portion 12 is pushed and deformed by the release pin 61 after an external force being applied to the release pin 61 from both arrow directions in FIG. 14A. Fitting of the sealing portion 12 and the notched portion 21 provided in the container 11 is released by the deformation of the claw 22 and, as shown in FIG. 14B, a stress is generated in the arrow direction in FIG. 14B with respect to the sealing portion 12. As a result, only the sealing portion 12 moves in a detachment direction so that only the sealing portion 12 can smoothly be removed from the container 11.

By including the sealing release mechanism 6 in the electric measuring apparatus 10 according to the present technology, risks of giving an unnecessary shock to the cartridge for electric measurement 1 or applying an extra external force to the container 11 or the sealing portion 12 are reduced. If only the sealing portion 12 can smoothly be removed thanks to the sealing release mechanism 6 and the reagent R is held in the sample holding portion 112, the reagent R can be prevented from flying to the cartridge wall surface and the like. As a result, improvements of the convenience of the user and the accuracy of measurement are realized.

(5) Others

In addition, the electric measuring apparatus 10 may include a positioning mechanism of the cartridge for electric measurement 1. By correctly setting the position of the cartridge for electric measurement 1, the contact position between the electrode 13 and the application unit 4 is also made correct and improvements of the convenience of the user and the accuracy of measurement are realized. Though not illustrated, for example, a method of designing a pin that positions the cartridge for electric measurement 1 in a height direction with respect to the electric measuring apparatus 10 can be cited.

Further, the electric measuring apparatus 10 can include, like the eleventh embodiment shown in FIG. 12, a positioning mechanism 7 of the release pin 61. By including the positioning mechanism 7 of the release pin 61, when the cartridge for electric measurement 1 includes the clamping mechanism 2, the sealing release mechanism 6 can be operated more correctly depending on the form of the clamping mechanism 2 or differences of flexibility of materials used. As a result, improvements of the convenience of the user and the accuracy of measurement are realized. More specifically, for example, a method of designing the positioning of the release pin 61 by installing a pair of positioning blocks 71 on the opposite side of the side on which the release pin 61 comes into contact with the cartridge for electric measurement 1, installing a positioning pin 72 between the pair of positioning blocks 71, and moving the positioning blocks 71 and the positioning pin 72 appropriately can be cited.

In addition, the electric measuring apparatus 10 may include an analysis unit that receives electric characteristic data of the sample S derived by the measuring unit 5 and determines physical properties of the sample S. However, the analysis unit is not indispensable in the electric measuring apparatus 10 according to the present technology and, for example, an analysis of electric characteristic data measured by the measuring unit 5 can be carried out by using an external computer. More specifically, electric characteristic data of the sample S derived by the measuring unit 5 is given to the analysis unit at measuring intervals and the analysis unit starts to determine physical properties of the sample S after receiving the electric characteristic data given by the measuring unit 5. In addition, the analysis unit makes the notification of results of properties determination of the sample S and/or dielectric constant data. The notification can be made by, for example, displaying results on a monitor as a graph or printing results on predetermined media.

3. Kit for Electric Measurement K

FIG. 15 is a schematic diagram schematically showing the first embodiment of the kit for electric measurement K according to the present technology. In the present embodiment, the cartridge for electric measurement 1 according to the aforementioned tenth embodiment is used. The kit for electric measurement K according to the present technology roughly includes at least the aforementioned cartridge for electric measurement 1 and a member for sample introduction 8. The cartridge for electric measurement 1 is as described above and the description thereof is omitted here.

(1) Member for Sample Introduction 8

The member for sample introduction 8 is a member that introduces the sample S into the container 11. For example, as shown in FIG. 15, a pipet-like chip 81 can be cited. For example, the aforementioned electric measuring apparatus 10 is provided with a suction mechanism (for example, a pipetter) and the chip 81 is mounted on the suction mechanism to be able to introduce the sample S.

The member for sample introduction 8 is not limited to the pipet-like chip 81 illustrated in FIG. 15 and a member of any form as the whole or a portion of an instrument capable of introducing the sample S into the container 11 may be adopted. For example, in addition to the pipet-like chip, an injection needle can be cited.

Like the cartridge for electric measurement 1, the member for sample introduction 8 can be made a single-use member. By making the member for sample introduction 8 a single-use member, time and effort to clean the tool used to introduce the sample can be saved and measurements can be made more efficient. In addition, an occurrence of measurement errors due to another sample S remaining in the tool used to introduce the sample can be prevented so that the accuracy of measurement can be improved.

4. Electric Measuring Method

The cartridge for electric measurement 1 according to the present technology can suitably be used for measurement of electric characteristics of the sample S. Electric characteristics that can be measured by the electric measuring method according to the present technology are not particularly limited and measurements can freely be made in accordance with the type of the sample S to be measured and physical properties to be analyzed. For example, the dielectric constant or impedance can be measured.

For example, when the target to be measured is blood, blood coagulation conditions or erythrocyte sedimentation rate conditions can be analyzed from measured values of dielectric constant or impedance by using the electric measuring method according to the present technology. More specifically, blood coagulation conditions or erythrocyte sedimentation rate conditions can be analyzed by, for example, extracting parameters showing respective characteristics from a plurality of measured values of the dielectric constant and/or impedance received in an analysis period and comparing the parameters and reference values defining the reference of the enhancement of blood coagulation capacity or the erythrocyte sedimentation rate progress.

It should be understood by those skilled in the art that various modifications, combinations, sub-combinations and alterations may occur depending on design requirements and other factors insofar as they are within the scope of the appended claims or the equivalents thereof.

The present technology can adopt the configuration as described below:

(1) A cartridge comprising:
  a container comprising an opening and a holding portion to hold a sample and/or a reagent;
  an electrode disposed on a container wall of the container; and
  a removable separator to separate at least some of the holding portion of the container from the electrode when the removable separator is inserted into the holding portion.

(2) The cartridge of (2), wherein the electrode is integrally formed with the container wall and is at a fixed position on the container wall.

(3) The cartridge of (1) or (2), wherein:
  the container wall comprises a location having a planar shape; and
  the electrode is disposed at the location having the planar shape.

(4) The cartridge of any one of (1) to (3), wherein a part of the electrode extending through the container wall to the holding portion is flush with an interior of the container wall.

(5) The cartridge of any one of (1) to (4), wherein the removable separator is at least partially disposed within the container and forms a liquid-tight seal with the container wall to separate the at least some of the holding portion from the electrode.

(6) The cartridge of (5),
  wherein the liquid-tight seal separates the sample and/or the reagent from the electrode.

(7) The cartridge of any one of (1) to (6), wherein:
  the opening of the container is on a top of the container; and a shape of the container comprises a gradient, spreading from a container bottom to the opening, on at least a portion of an interior of the container wall of the container.

(8) The cartridge of any one of (1) to (7), wherein a shape of the removable separator comprises a gradient, spreading from a bottom of the removable separator toward a top of the removable separator, on at least a portion of an exterior of a wall of the removable separator.

(9) The cartridge of (8), wherein:
the gradient of the portion of the interior of the container wall is equivalent to the gradient of the portion of the exterior of the wall of the removable separator; and
when inserted into the container, the removable separator is subject to stress toward a top of the container.

(10) The cartridge of any one of (1) to (9), further comprising a clamp that fixes relative positions of the container and the removable separator when the removable separator is inserted into the holding portion and separates the at least some of the holding portion from the electrode.

(11) The cartridge of (10), wherein the clamp is arranged to be released from clamping and to be incapable of re-clamping after release.

(12) The cartridge of (10) or (11), wherein:
the clamp comprises a notched portion provided in the container and a claw provided on the removable separator and arranged to catch in the notched portion when the removable separator is inserted into the holding portion;
the claw is flexible;
the clamp is arranged to be released from clamping by deforming the claw or cutting the claw to a state in which the notched portion does not catch in the notched portion following release.

(13) The cartridge of any one of (1) to (12), wherein a bottom of the removable separator comprises a hole that is open when the removable separator is not inserted into the holding portion and is closed when the removable separator is inserted into the holding portion to separate the at least some of the holding portion of the container from the electrode.

(14) The cartridge of any one of (1) to (13), wherein the electrode is disposed in the holding portion.

(15) The cartridge of any one of (1) to (14), wherein the container wall comprises a first side and a second side opposite the first side;
the electrode is disposed on the first side; and
the cartridge further comprises an opposite electrode disposed on the second side.

(16) The cartridge of any one of (1) to (15), wherein the electrode is configured to apply an electrical signal to the sample and/or the reagent.

(17) The cartridge of any one of (1) to (16), wherein the container and/or the removable separator comprises a resin selected from a group of resins consisting of polypropylene, polystyrene, acrylic, and polysulfone.

(18) The cartridge of any one of (1) to (17) in a kit, the kit further comprising a member to introduce the sample into the container.

(19) The kit of (18), wherein the member is a pipet.

(20) The kit of (18), wherein the member is an injection needle.

(21) An electric measuring apparatus comprising:
a cartridge comprising:
a container comprising an opening and a holding portion to hold a sample and/or a reagent;
an electrode disposed on a container wall of the container and configured to apply an electrical signal to the sample and/or the reagent; and
a removable separator to separate at least some of the holding portion of the container from the electrode when the removable separator is inserted into the holding portion; a cartridge holder into which the cartridge is inserted;
a signal generating circuit to generate a first signal to be applied to the electrode of the cartridge; and
a measuring circuit to measure at least one electrical characteristic of a second signal, resulting from application of the first signal to the electrode of the cartridge, indicative of one or more electrical characteristics of the sample and/or the reagent disposed in the holding portion.

(22) The electric measuring apparatus of (21), wherein the electrode is disposed in the holding portion.

(23) The electric measuring apparatus of (21) or (22), wherein the container wall comprises a first side and a second side opposite the first side;
the electrode is disposed on the first side; and
the cartridge further comprises a second electrode disposed on the second side.

(24) The electric measuring apparatus of any one of (21) to (23), wherein:
the cartridge further comprises a clamp, the clamp comprising a notched portion provided in the container and a claw provided on the removable separator and arranged to catch in the notched portion when the removable separator is inserted into the holding portion; and
the cartridge holder further comprises a sealing release member to, upon insertion of
the cartridge into the cartridge holder, release the claw of the clamp from the notched portion.

(25) A method comprising:
removing a removable separator from a container of a cartridge, the cartridge comprising a sample and/or a reagent disposed in the container and an electrode at least partially disposed in the container, wherein prior to removal the removable separator formed a liquid-tight seal separating the sample and/or the reagent from the electrode;
applying at least one electrical signal to the electrode of the cartridge;
measuring at least one second signal resulting from application of the at least one electrical signal to the electrode of the cartridge; and
determining at least one diagnostic result of a sample disposed with the sample and/or the reagent in the container based at least in part on the measuring.

Furthermore, the present technology can adopt the configuration as described below:

[1'] A cartridge for electric measurement comprising:
a container including an opening and a sample holding portion;
a sealing portion that seals at least a portion of the sample holding portion; and
an electrode fixed to the sample holding portion, wherein the sealing portion separates a sealed portion of the sample holding portion and the electrode.

[2'] The cartridge for electric measurement according to [1'], wherein the container has a gradient spreading from a container bottom to the opening on at least a portion of an inner wall.

[3'] The cartridge for electric measurement according to [1'] or [2'], wherein the sealing portion has a gradient spreading from a bottom of the sealing portion to an upper portion of the sealing portion on at least a portion of an outer wall.

[4'] The cartridge for electric measurement according to any one of [1'] to [3'], wherein the sealing portion is subject to a stress in a sealing release direction from the container.

[5'] The cartridge for electric measurement according to any one of [1'] to [4], wherein at least a portion of an inner wall of the container and at least a portion of an outer wall of the sealing portion have a gradient spreading from a bottom to the opening, and
the gradient of the outer wall of the sealing portion is equivalent to the gradient of the inner wall of the container or more.

[6'] The cartridge for electric measurement according to any one of [1'] to [5'], further comprising:
a clamping mechanism that fixes the container and the sealing portion when the sealing portion seals at least a portion of the sample holding portion.

[7'] The cartridge for electric measurement according to [6'], wherein the clamping mechanism is made difficult to re-fix after fixing is released.

[8'] The cartridge for electric measurement according to [6'] or [7'], wherein the clamping mechanism includes
a notched portion provided in the container, and
a claw fitted into the notched portion and provided in the sealing portion.

[9'] The cartridge for electric measurement according to [8'], wherein the claw has flexibility.

[10'] The cartridge for electric measurement according to [8'] or [9'], wherein the claw is deformed or cut to a form in which re-fixing is difficult when fixing is released.

[11'] The cartridge for electric measurement according to any one of [1'] to [10'], wherein the sealing portion is provided with a through hole that is opened when the sample holding portion is in a non-sealed state and closed when at least a portion of the sample holding portion is in a sealed state.

[12'] The cartridge for electric measurement according to any one of [1'] to [11'], wherein the container and the sealing portion are formed from a resin.

[13'] The cartridge for electric measurement according to [12'], wherein the resin is one resin or more selected from polypropylene, polystyrene, acrylic, and polysulfone.

[14'] The cartridge for electric measurement according to any one of [1'] to [13'], wherein the sample holding portion has a reagent encapsulated in the sealed portion.

[15'] The cartridge for electric measurement according to [14'], wherein the reagent is liquid.

[16'] The cartridge for electric measurement according to any one of [1'] to [15'], wherein the sample is a biological sample.

[17'] An electric measuring apparatus comprising:
a container including an opening and a sample holding portion;
a sealing portion that seals at least a portion of the sample holding portion and;
an electrode fixed to the sample holding portion, wherein the sealing portion at least includes
a cartridge for electric measurement that separates a sealed portion of the sample holding portion and the electrode,
a cartridge insertion portion through which the cartridge for electric measurement is inserted,
an application unit that applies a voltage to the electrode, and
a measuring unit that measures electric characteristics of the sample.

[18'] The electric measuring apparatus according to [17'], further comprising: a sealing release mechanism that releases a sealed state of at least a portion of the sample holding portion.

[19'] A kit for electric measurement comprising:
a container including an opening and a sample holding portion;
a sealing portion that seals at least a portion of the sample holding portion and;
an electrode fixed to the sample holding portion, wherein the sealing portion includes
a cartridge for electric measurement that separates a sealed portion of the sample holding portion and the electrode, and
a member for sample introduction that introduces the sample into the container.

[20'] An electric measuring method for measuring electric characteristics of a sample by using a cartridge for electric measurement comprising:
a container including an opening and a sample holding portion;
a sealing portion that seals at least a portion of the sample holding portion and;
an electrode fixed to the sample holding portion, wherein when at least a portion of the sample holding portion is sealed by the sealing portion, a sealed portion of the sample holding portion and the electrode are separated by the sealing portion.

REFERENCE SIGNS LIST

1 Cartridge for electric measurement
11 Container
111 Opening
112 Sample holding portion
113 Container bottom
12 Sealing portion
121 Bottom of the sealing portion
122 Upper portion of the sealing portion
123 Through hole
124 Packing
13 Electrode
2 Clamping mechanism
21 Notched portion
22 Claw
S Sample
R Reagent
10 Electric measuring apparatus
3 Cartridge insertion portion
4 Application unit
5 Measuring unit
6 Sealing release mechanism
61 Release pin
7 Positioning mechanism of the release pin 61
71 Positioning block
72 Positioning pin
K Kit for electric measurement
8 Member for sample introduction
81 Pipet-like chip 81

The invention claimed is:

1. A cartridge comprising:
a container comprising an opening and a holding portion to hold a sample and/or a reagent;

an electrode disposed on a container wall of the container;
a removable separator to separate at least some of the holding portion of the container from the electrode when the removable separator is inserted into the holding portion; and
a clamp that fixes relative positions of the container and the removable separator when the removable separator is inserted into the holding portion and separates the at least some of the holding portion from the electrode, wherein:
the clamp comprises a notched portion provided in the container and a claw provided on the removable separator and arranged to catch in the notched portion when the removable separator is inserted into the holding portion;
the claw is flexible;
the clamp is arranged to be released from clamping by deforming the claw or cutting the claw to a state in which the claw does not catch in the notched portion following release.

2. The cartridge of claim 1, wherein the electrode is integrally formed with the container wall and is at a fixed position on the container wall.

3. The cartridge of claim 1, wherein:
the container wall comprises a location having a planar shape; and
the electrode is disposed at the location having the planar shape.

4. The cartridge of claim 1, wherein a part of the electrode extending through the container wall to the holding portion is flush with an interior of the container wall.

5. The cartridge of claim 1, wherein the removable separator is at least partially disposed within the container and forms a liquid-tight seal with the container wall to separate the at least some of the holding portion from the electrode.

6. The cartridge of claim 5, wherein the liquid-tight seal separates the sample and/or the reagent from the electrode.

7. The cartridge of claim 1, wherein:
the opening of the container is on a top of the container; and
a shape of the container comprises a gradient, spreading from a container bottom to the opening, on at least a portion of an interior of the container wall of the container.

8. The cartridge of claim 7, wherein a shape of the removable separator comprises a gradient, spreading from a bottom of the removable separator toward a top of the removable separator, on at least a portion of an exterior of a wall of the removable separator.

9. The cartridge of claim 8, wherein:
the gradient of the portion of the interior of the container wall is equivalent to the gradient of the portion of the exterior of the wall of the removable separator; and
when inserted into the container, the removable separator is subject to stress toward a top of the container.

10. The cartridge of claim 1, wherein the clamp is arranged to be incapable of re-clamping after release.

11. The cartridge of claim 1, wherein a bottom of the removable separator comprises a hole that is open when the removable separator is not inserted into the holding portion and is closed when the removable separator is inserted into the holding portion to separate the at least some of the holding portion of the container from the electrode.

12. The cartridge of claim 1, wherein the electrode is disposed in the holding portion.

13. The cartridge of claim 1, wherein the container wall comprises a first side and a second side opposite the first side;
the electrode is disposed on the first side; and
the cartridge further comprises an opposite electrode disposed on the second side.

14. The cartridge of claim 1, wherein the electrode is configured to apply an electrical signal to the sample and/or the reagent.

15. The cartridge of claim 1, wherein the container and/or the removable separator comprises a resin selected from a group of resins consisting of polypropylene, polystyrene, acrylic, and polysulfone.

16. The cartridge of claim 1 in a kit, the kit further comprising a member to introduce the sample into the container.

17. The kit of claim 16, wherein the member is a pipet.

18. The kit of claim 16, wherein the member is an injection needle.

* * * * *